US010109802B2

(12) United States Patent
Siraj et al.

(10) Patent No.: US 10,109,802 B2
(45) Date of Patent: Oct. 23, 2018

(54) CARBAZOLE-BASED GUMBOS FOR HIGHLY EFFICIENT BLUE OLEDS

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Noureen Siraj, Baton Rouge, LA (US); Isiah Manuel Warner, Baton Rouge, LA (US); Thenahandi Prasanthi Deepthika De Silva, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 15/541,524

(22) PCT Filed: Jan. 5, 2016

(86) PCT No.: PCT/US2016/012211
§ 371 (c)(1),
(2) Date: Jul. 5, 2017

(87) PCT Pub. No.: WO2016/112027
PCT Pub. Date: Jul. 14, 2016

(65) Prior Publication Data
US 2018/0026201 A1 Jan. 25, 2018

Related U.S. Application Data

(60) Provisional application No. 62/099,720, filed on Jan. 5, 2015.

(51) Int. Cl.
H01L 35/24 (2006.01)
H01L 51/00 (2006.01)
(Continued)

(52) U.S. Cl.
CPC ........ *H01L 51/0072* (2013.01); *C07C 303/30* (2013.01); *C07C 303/40* (2013.01);
(Continued)

(58) Field of Classification Search
CPC .. H01L 51/0072; C07C 303/30; C07C 303/40
(Continued)

(56) References Cited

U.S. PATENT DOCUMENTS 8,808,880 B2 * 8/2014 Kim ..................... C07D 209/88
257/40
2007/0262704 A1 11/2007 Tsai et al.
(Continued)

FOREIGN PATENT DOCUMENTS

WO 2010043691 A1 4/2010
WO 2014147078 A1 9/2014

OTHER PUBLICATIONS

International Search Report for PCT/US2016/012211 dated Mar. 18, 2016.
(Continued)

*Primary Examiner* — David S Blum
(74) *Attorney, Agent, or Firm* — Thomas | Horstemeyer, LLP

(57) ABSTRACT

Various examples are provided for carbazole-based GUMBOS (group of uniform materials based on organic salts), and its application in organic light emitting diodes (OLEDs). In one example, a composition includes a solid phase carbazole-based GUMBOS (group of uniform materials based on organic salts) comprising a counterion such as, e.g., trifluoromethanesulfonate ([Otf]), bis-(trifluoromethanesul-
(Continued)

fonyl)imide ([NTf$_2$]), bis-(pentafluoroethylsulfonyl)imide ([BETI]), tetrafluoroborate (BF4), hexafluorophosphate (PF6), and/or thiocyanate (SCN). The carbazole-based GUMBOS can include carbazoleimidazole-based GUMBOS or 3,6-diBDC carbazolium-based GUMBOS. In another example, a method includes preparing a biphasic solution; separating a layer of DCM from the biphasic solution after stirring; washing the DCM with water to remove byproducts; and evaporating the DCM to form a solid phase carbazoleimidazole-based GUMBOS. Preparing the biphasic solution can include carbazoleimidazolium iodide (CM) dissolved in dichloromethane (DCM) and a dissolved salt including a sodium salt or a lithium salt.

25 Claims, 23 Drawing Sheets

(51) Int. Cl.
| | | |
|---|---|---|
| H01L 21/00 | (2006.01) | |
| C07C 309/66 | (2006.01) | |
| C07C 311/48 | (2006.01) | |
| C09K 11/06 | (2006.01) | |
| C07C 303/40 | (2006.01) | |
| C07C 303/30 | (2006.01) | |
| C07D 403/14 | (2006.01) | |
| C07D 403/04 | (2006.01) | |
| H01L 51/56 | (2006.01) | |
| H01L 51/52 | (2006.01) | |
| H01L 51/50 | (2006.01) | |

(52) U.S. Cl.
CPC .......... *C07C 309/66* (2013.01); *C07C 311/48* (2013.01); *C07D 403/04* (2013.01); *C07D 403/14* (2013.01); *C09K 11/06* (2013.01); *H01L 51/0067* (2013.01); *C09K 2211/1018* (2013.01); *H01L 51/0025* (2013.01); *H01L 51/5032* (2013.01); *H01L 51/5072* (2013.01); *H01L 51/5206* (2013.01); *H01L 51/5221* (2013.01); *H01L 51/56* (2013.01)

(58) Field of Classification Search
USPC ................................................ 257/40; 438/30
See application file for complete search history.

(56) References Cited

U.S. PATENT DOCUMENTS

| | | |
|---|---|---|
| 2011/0217553 A1 | 9/2011 | Warner et al. |
| 2013/0035509 A1 | 2/2013 | Schmid et al. |
| 2014/0001442 A1* | 1/2014 | Lee ............ C07F 7/0816 257/40 |
| 2014/0073798 A1 | 3/2014 | Li et al. |

OTHER PUBLICATIONS

Siraj et al. "Carbazole-Derived Group of Uniform Materials Based on Organic Salts: Solid State Fluorescent Analogues of Ionic Liquids for Potential Applications in Organic-Based Blue Light-Emitting Diodes", J. Phys. Chem. C 2014, vol. 118, pp. 2312-2320 (Published: Jan. 9, 2014].

* cited by examiner

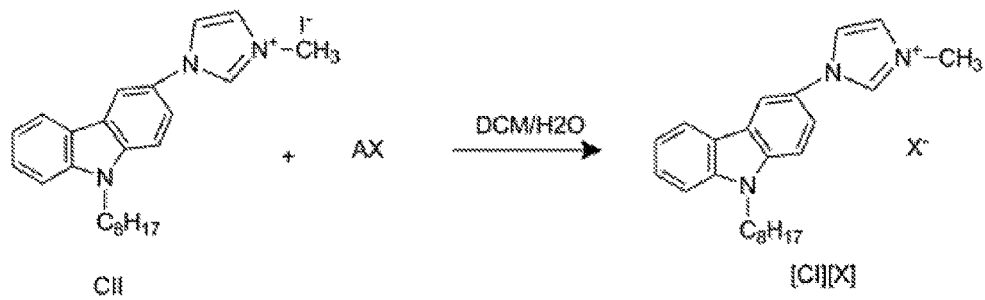
Where X is
[OTf]-
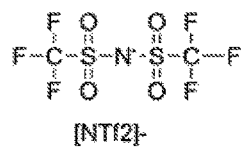
[NTf2]-
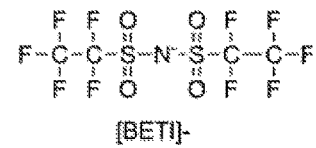
[BETI]-
FIG. 1A
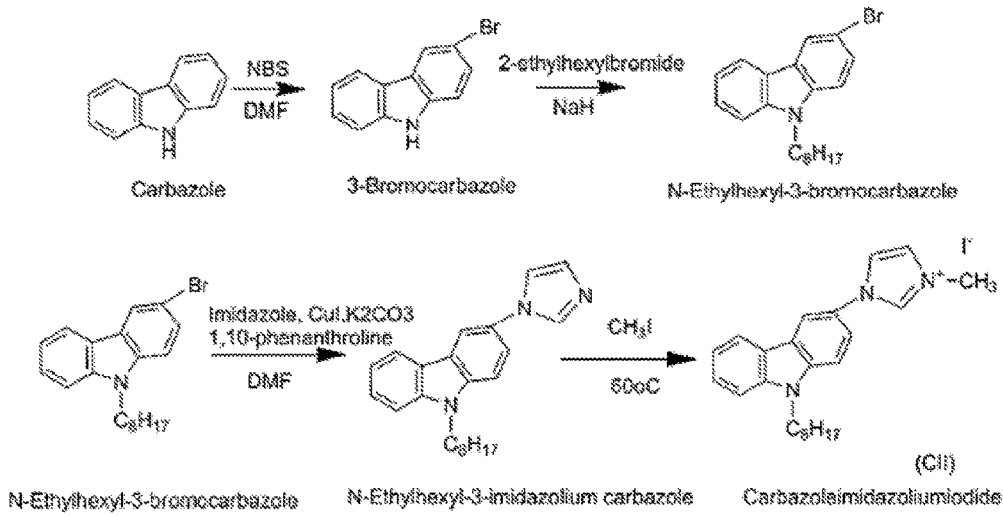
FIG. 1B
| GUMBOS | T_d/°C |
|---|---|
| CII | 310 |
| [CI][OTf] | 395 |
| [CI][NTf₂] | 432 |
| [CI][BETI] | 417 |
FIG. 2

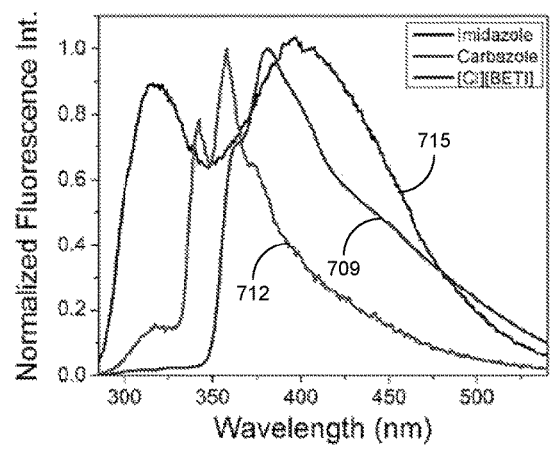
FIG. 7C
| GUMBOS | solvent | $\lambda_{abs}$/nm | $\varepsilon/10^4\,M^{-1}cm^{-1}$ | $\lambda_{flow}$/nm | % $\phi_{fl}$ |
|---|---|---|---|---|---|
| CII | MeOH | 275 | | 380 | 25 |
| | DCM | 280 | 2.34 | 440 | 28 |
| [CII][OTf] | MeOH | 273 | 1.51 | 378 | |
| | DCM | 280 | 6.75 | 440 | 94 |
| [CII][NTf₂] | MeOH | 273 | | 380 | |
| | DCM | 281 | 9.52 | 440 | 73 |
| [CII][BETI] | MeOH | 273 | 2.60 | 378 | |
| | DCM | 280 | 1.68 | 440 | 99 |
FIG. 8
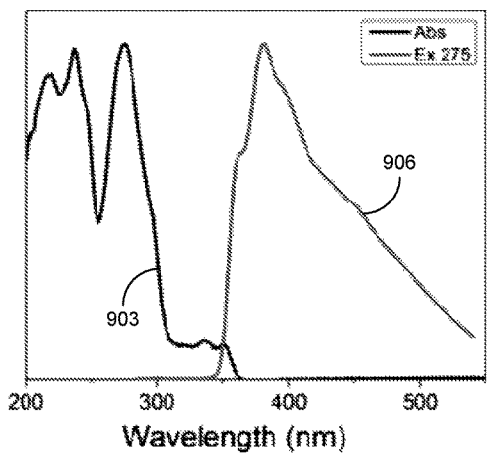
FIG. 9A

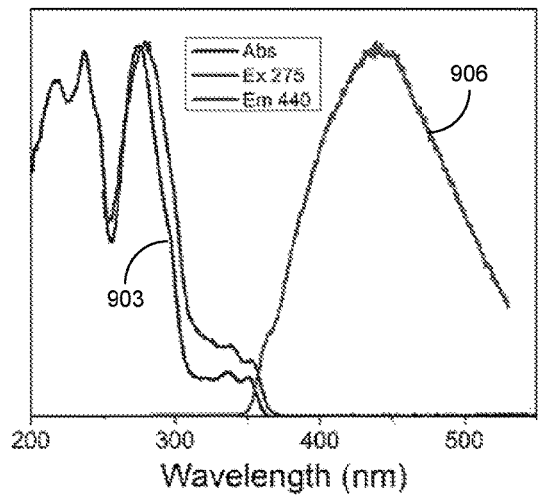
FIG. 9B
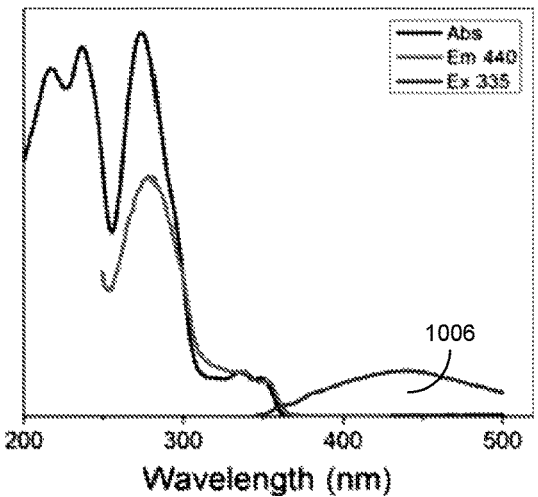
FIG. 10
| GUMBOS | $\tau_1$/ns | $\alpha_1$ | $\tau_2$/ns | $\alpha_2$ | $\tau_{avg}$/ns | $\chi_{red}^2$ |
|---|---|---|---|---|---|---|
| [CI][OTf] | 3.379 | 0.07 | 6.649 | 0.93 | 6.428 | 1.032 |
| [CI][NTf$_2$] | 1.903 | 0.06 | 6.624 | 0.94 | 6.348 | 1.021 |
| [CI][BETI] | 3.414 | 0.07 | 6.659 | 0.93 | 6.445 | 1.020 |
FIG. 11A
| GUMBOS | $\tau_1$/ns | $\alpha_1$ | $\tau_2$/ns | $\alpha_2$ | $\tau_{avg}$/ns | $\chi_{red}^2$ |
|---|---|---|---|---|---|---|
| [CI][OTf] | 0.133 | 0.481 | 1.640 | 0.029 | 2.480 | 1.008 |
| [CI][NTf$_2$] | 0.131 | 0.510 | 1.607 | 0.026 | 2.361 | 1.018 |
| [CI][BETI] | 0.094 | 0.626 | 1.485 | 0.020 | 1.799 | 1.018 |
FIG. 11B

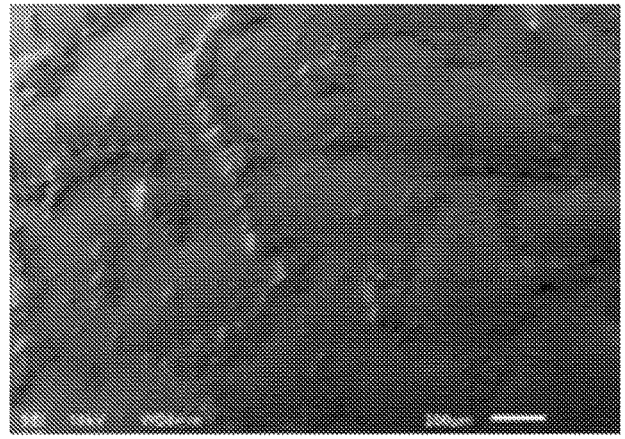
FIG. 12A
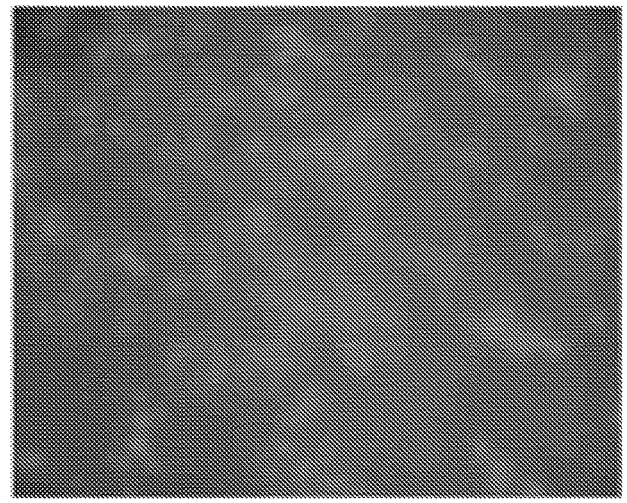
FIG. 12B
| GUMBOS | $\lambda_{abs}$/nm solution (film) |
|---|---|
| [CI][OTf] | 378 (385) |
| [CI][NTf$_2$] | 380 (389) |
| [CI][BETI] | 378 (392) |
FIG. 13A

| GUMBOS | $E$ vs Fc/V | HOMO/eV | LUMO/eV | $E_g^a$/eV | $E_g^b$/eV |
|---|---|---|---|---|---|
| CII | 0.96 | −5.76 | −2.36 | 3.42 | |
| [CII][OTf] | 0.94 | −5.74 | −2.32 | 3.41 | 3.77/4.4 |
| [CII][NTf₂] | 0.95 | −5.75 | −2.36 | 3.39 | 3.74/4.3 |
| [CII][BETI] | 0.93 | −5.73 | −2.31 | 3.42 | 3.58/4.1 |
$^a$Band gap is calculated by using onset wavelength.
$^b$Band gap is calculated by computational calculation, TDDFT/DFT.
FIG. 16B
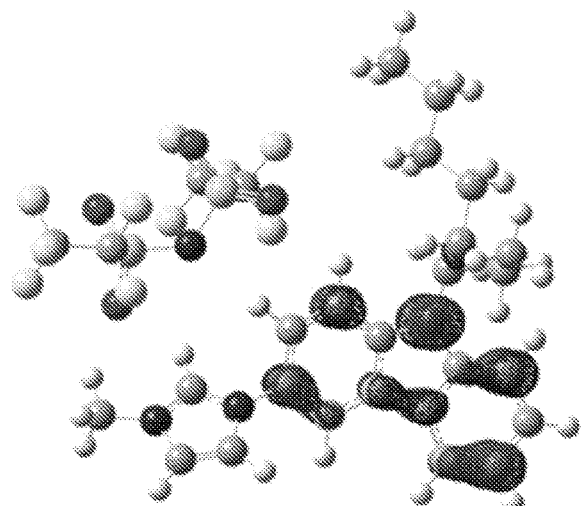
FIG. 17A
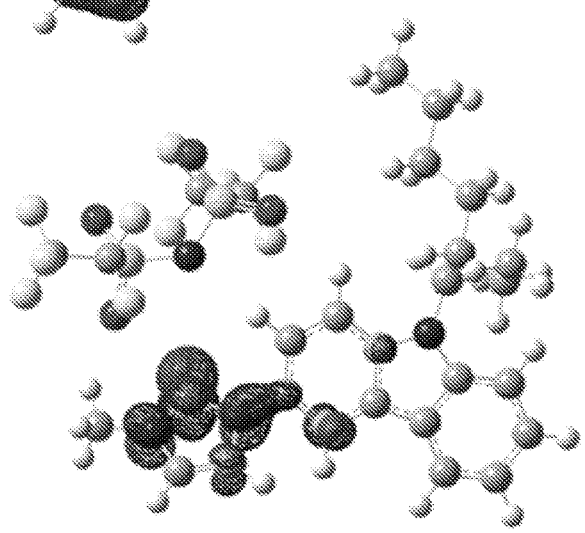
FIG. 17B

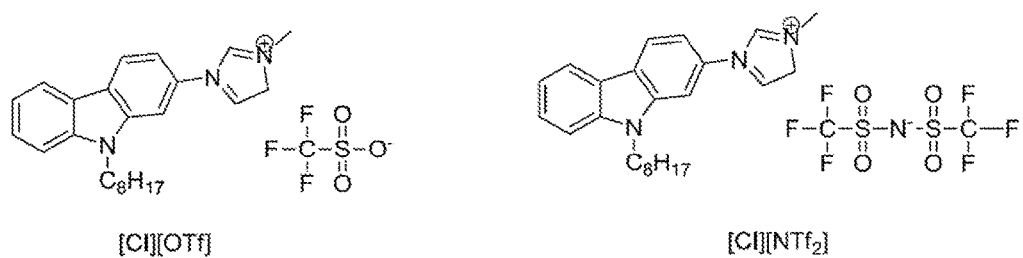
FIG. 18
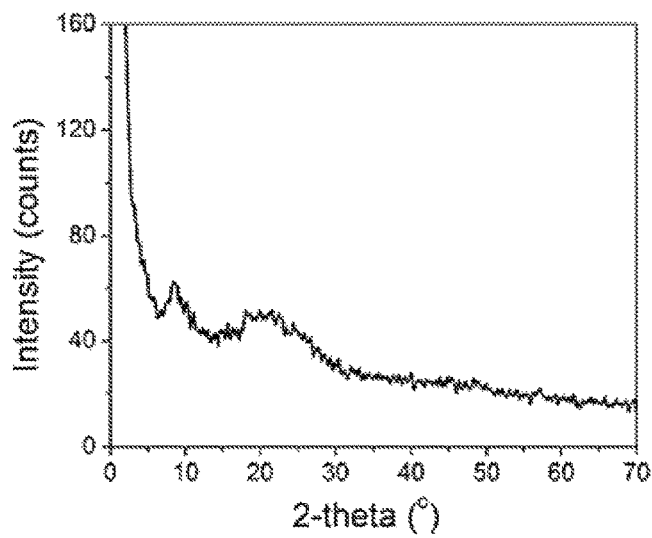
FIG. 19A
| ILs | $T_d/°C$ | $T_m/°C$ |
|---|---|---|
| CII | 310 | 190 |
| [CII][OTf] | 395 | 56 |
| [CII][NTf$_2$] | 432 | <100 |
FIG. 19B

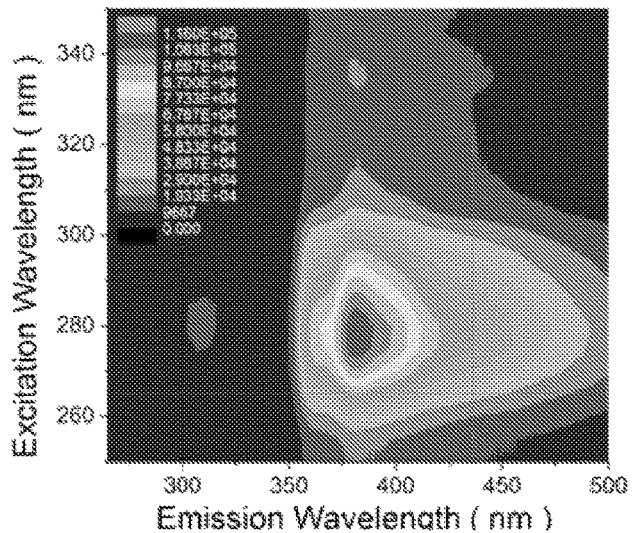
FIG. 22
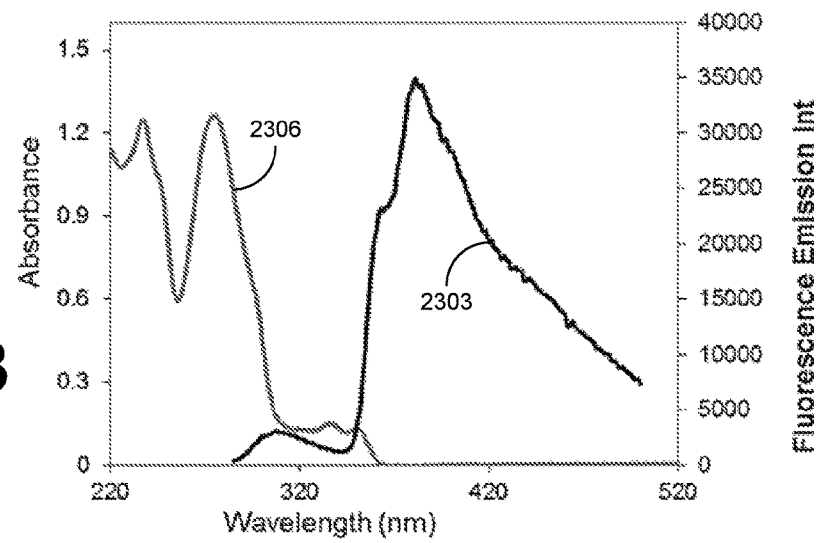
FIG. 23
| sample | $\lambda_{ex}/\lambda_{em}$ (nm) | $\alpha_1$ | $\tau_1$ (ns) | $\alpha_2$ | $\tau_2$ (ns) | $\alpha_3$ | $\tau_3$ (ns) | $\tau_{avg}$ (ns) | $\chi_{red}^2$ |
|---|---|---|---|---|---|---|---|---|---|
| [CI][OTf] | 277/309 | 0.36 | 0.985 | 0.55 | 3.095 | 0.09 | 8.014 | 2.76 | 1.042 |
| [CI][OTf] | 277/362 | 0.11 | 0.857 | 0.08 | 3.658 | 0.81 | 8.316 | 7.15 | 1.029 |
| [CI][OTf] | 344/385 | 0.09 | 0.691 | 0.18 | 3.234 | 0.73 | 8.12 | 6.558 | 1.013 |
| [CI][NTf$_2$] | 277/309 | 0.32 | 1.139 | 0.63 | 3.804 | 0.05 | 9.331 | 3.236 | 1.027 |
| [CI][NTf$_2$] | 277/362 | 0.18 | 0.915 | 0.38 | 4.521 | 0.44 | 9.558 | 6.886 | 1.044 |
| [CI][NTf$_2$] | 344/385 | 0.72 | 0.072 | 0.06 | 2.089 | 0.22 | 8.231 | 1.978 | 1.066 |
FIG. 24

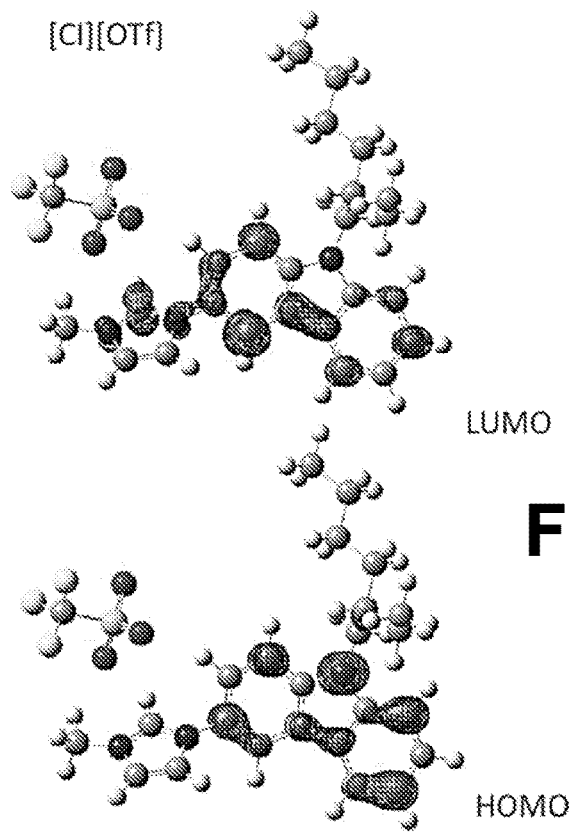
FIG. 25A
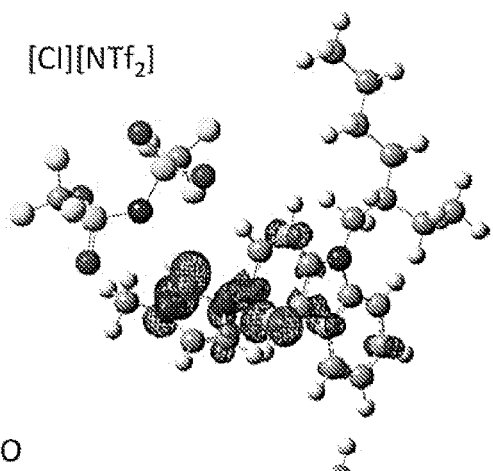
FIG. 25B
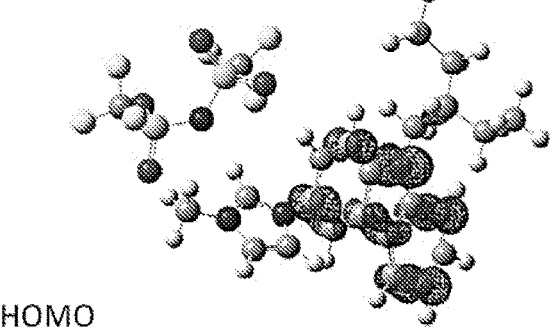

| Compound | TDDFT excitation energies (eV) | Excitation wavelength (nm) | Oscillator strength (f) | Major contribution |
|---|---|---|---|---|
| [CI][OTf] | 3.77 | 328.40 | 0.023 | H→L (0.67) |
| | 4.34 | 285.51 | 0.327 | H-1→L (0.46) |
| [CI][NTf₂] | 3.74 | 331.43 | 0.031 | H→L (0.64) |
| | 4.23 | 292.75 | 0.234 | H-L→L (0.64) |

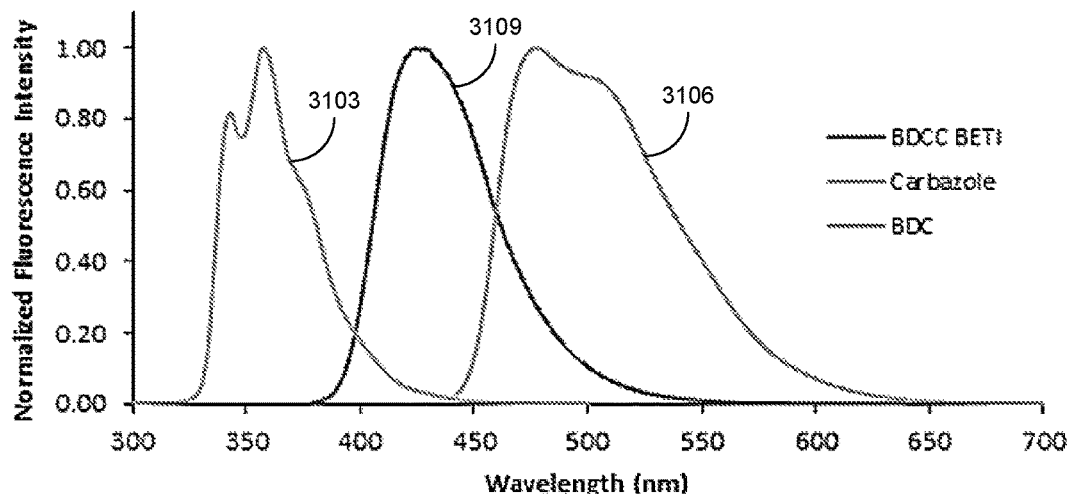
FIG. 31
| Compound | Eg (eV) | E_HOMO (eV) | E_LUMO (eV) | QY | T_D (°C) |
|---|---|---|---|---|---|
| BDCC BETI | 3.01 | 5.03 | 2.02 | 96 | 311 |
| BDCC NTF2 | 3.01 | 5.04 | 2.03 | 87 | 308 |
| BDCC OTF | 3.02 | 5.00 | 1.98 | 91 | 255 |
| BDCC Iodide | 3.06 | 5.08 | 2.02 | 90 | 188 |
FIG. 32
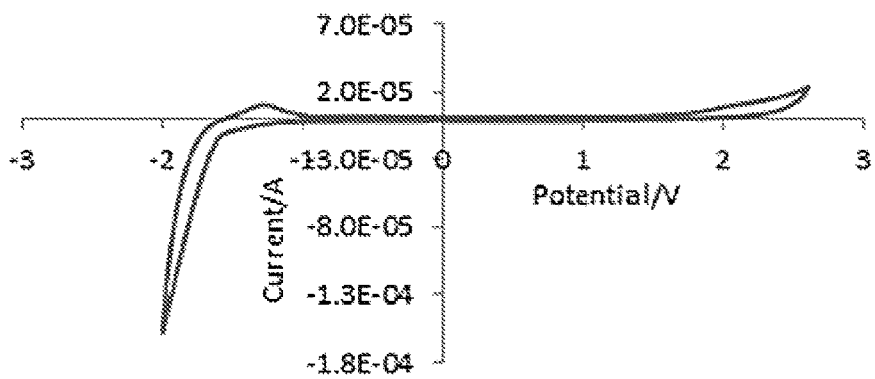
FIG. 33A

US 10,109,802 B2

CARBAZOLE-BASED GUMBOS FOR HIGHLY EFFICIENT BLUE OLEDS

CROSS REFERENCE TO RELATED APPLICATIONS

This application is the 35 U.S.C. § 371 national stage application of PCT Application No. PCT/US2016/012211, filed Jan. 5, 2016, which claims priority to, and the benefit of, U.S. provisional application entitled "CARBAZOLE BASED GUMBOS FOR HIGHLY EFFICIENT BLUE OLEDS" having Ser. No. 62/099,720, filed Jan. 5, 2015, both of which are hereby incorporated by reference in their entireties.

STATEMENT REGARDING FEDERALLY SPONSORED RESEARCH OR DEVELOPMENT

This invention was made with government support under agreements CHE-1243916 and CHE-1307611 awarded by the National Science Foundation. The Government has certain rights to the invention.

BACKGROUND

Over the last several decades, ionic liquids (ILs) have gained increasing interest of researchers due to their unusual and applicable properties. These molecules have been used in many different fields to replace conventional organic solvents and have also been referred to as green solvents due to their low volatility. The general tunability of these molecules has led to emergence of task-specific ionic liquids that are designed to incorporate desired characteristics for specific applications.

SUMMARY

Embodiments of the present disclosure are related to carbazole-based GUMBOS (group of uniform materials based on organic salts), which can be included in organic light emitting diodes (OLEDs).

In one embodiment, among others, a composition includes a solid phase carbazole-based GUMBOS comprising a carbazole-based counterion. The carbazole-based counterion can be trifluoromethanesulfonate ([OTf]), bis-(trifluoromethanesulfonyl)imide ([NTf$_2$]), bis-(pentafluoroethylsulfonyl)imide ([BETI]), tetrafluoroborate (BF4), hexafluorophosphate (PF6), and/or thiocyanate (SCN). The carbazole-based GUMBOS can include an imidazole group or (alkyl)imidazole group at a 3-, 6-, or N-position of a carbazole unit. The (alkyl)imidazole group can be a (methyl) imidazole group. The carbazole-based GUMBOS can include carbazoleimidazolium trifluoromethanesulfonate [CI][OTf], carbazoleimidazolium bis-(trifluoromethylsulfonyl) imide [CI][NTf$_2$], or carbazoleimidazolium bis(pentafluoroethylsulfonyl)imide [CI][BETI]. The carbazole-based GUMBOS can include carbazole-coumarin conjugated organic semiconducting small ionic compounds.

Carbazole-based GUMBOS can have a fluorescence quantum yield of about 73% or greater, about 94% or greater, or about 99%. The carbazole-based GUMBOS can have a thermal decomposition temperature (Td) in a range from about 350° C. to about 500° C. The carbazole-based GUMBOS can exhibit radiative emission from a second excited singlet state and/or from a first excited singlet state. An energy gap between a first excited singlet state ($S_1$) and a second excited singlet state ($S_2$) of the carbazole-based GUMBOS can be greater than 6000 cm$^{-1}$.

In an embodiment, an organic light emitting diode (OLED) includes an active layer including carbazole-based GUMBOS. The carbazole-based GUMBOS can be in a solid phase. The active layer can be disposed between a first electrode and a second electrode, and can include a GUMBOS emission layer and an electron transport layer.

In an embodiment, carbazoleimidazole-based GUMBOS can be made by preparing a biphasic solution comprising carbazoleimidazolium iodide (CII) dissolved in dichloromethane (DCM) and a dissolved salt comprising a sodium salt or a lithium salt. A layer of DCM can be separated from the biphasic solution after stirring. For example, the biphasic solution can be stirred for 3-4 days. The DCM can be washed with water (e.g., deionized water) to remove byproducts and evaporated to form a solid phase carbazoleimidazole-based GUMBOS, which can be freeze dried to remove small amounts of water.

The dissolved salt can comprise sodium trifluoromethanesulfonate (NaOTf) dissolved in deionized water, lithium bis(trifluoromethylsulfonyl)imide (LiNTf$_2$) dissolved in deionized water, or lithium bis-(pentafluoroethylsulfonyl) imide (LiBETI) dissolved in deionized water. The carbazoleimidazole-based GUMBOS can be based upon anion exchange of N-Ethylhexyl-3-imidazolium carbazole iodide.

Other compositions, devices, systems, methods, features, and advantages of the present disclosure will be or become apparent to one with skill in the art upon examination of the following drawings and detailed description. It is intended that all such additional compositions, devices, systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A and 1B are schematic representations illustrating an example of the synthesis protocol for carbazole-based GUMBOS, in accordance with various embodiments of the present disclosure.

FIG. 2 is a table illustrating anion-dependent decomposition temperatures for carbazole-based GUMBOS, in accordance with various embodiments of the present disclosure.

FIGS. 7A through 7C illustrate examples of fluorescence emission spectra of CII, [CI][OTf], [CI][NTf$_2$] and [CI]

[BETI] in methanol, in accordance with various embodiments of the present disclosure.

FIG. 8 is a table illustrating absorption, emission wavelength, molar extinction coefficients, and quantum yields of carbazole-based GUMBOS, in accordance with various embodiments of the present disclosure.

FIGS. 9A and 9B illustrate examples of absorption and fluorescence emission spectra of [CI][BETI] in DCM, in accordance with various embodiments of the present disclosure.

FIG. 10 illustrates an example of absorption, excitation, and emission spectra of [CI][BETI] in DCM, in accordance with various embodiments of the present disclosure.

FIGS. 11A and 11B are tables illustrating lifetime data of carbazole-based GUMBOS in DCM and methanol, in accordance with various embodiments of the present disclosure.

FIGS. 12A and 12B are an scanning electron microscope (SEM) image and an epifluorescence image of a [CI][BETI] film deposited on quartz, in accordance with various embodiments of the present disclosure.

FIG. 13A is a table illustrating fluorescence emission maxima of carbazole-based GUMBOS, in accordance with various embodiments of the present disclosure.

Figure 13B:
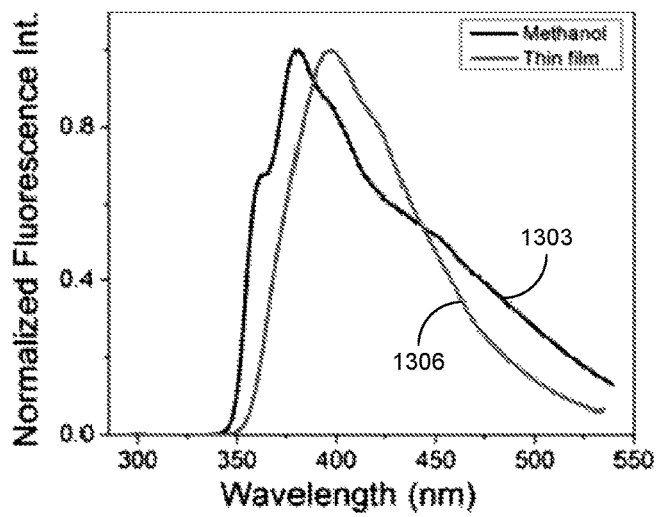

FIG. 13B illustrates examples of fluorescence emission of [CI][NTf$_2$], in accordance with various embodiments of the present disclosure.

Figure 14:
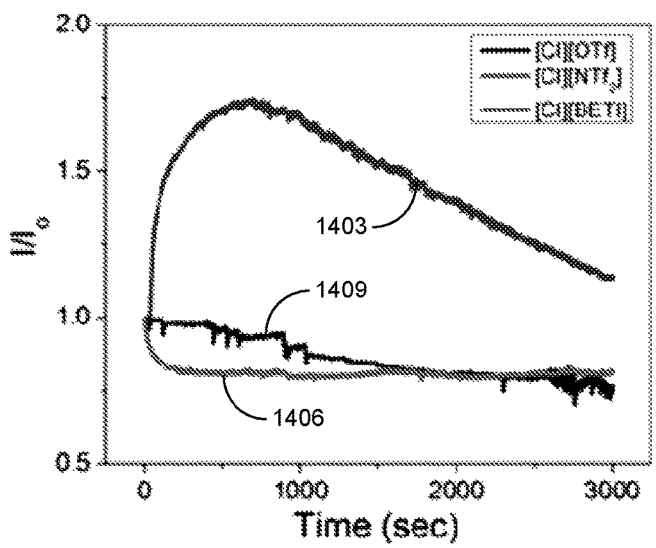

FIG. 14 illustrates examples of photostability of carbazole-based GUMBOS, in accordance with various embodiments of the present disclosure.

Figure 15A:
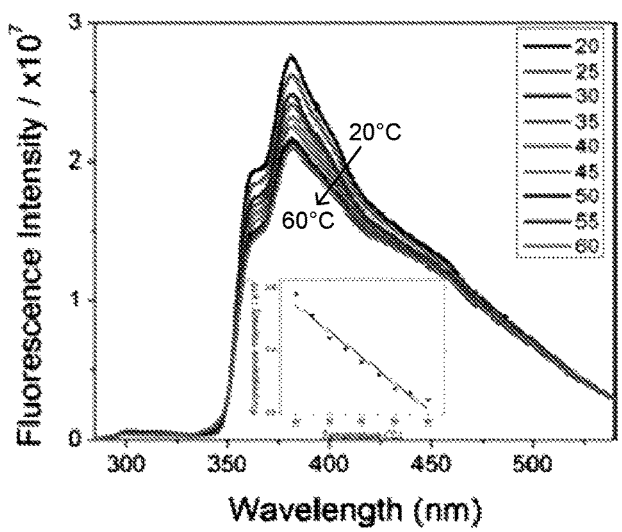
Figure 15B:
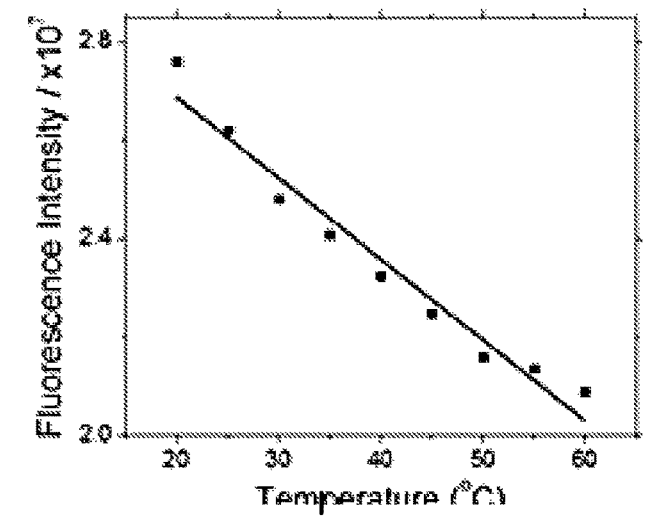
Figure 15C:
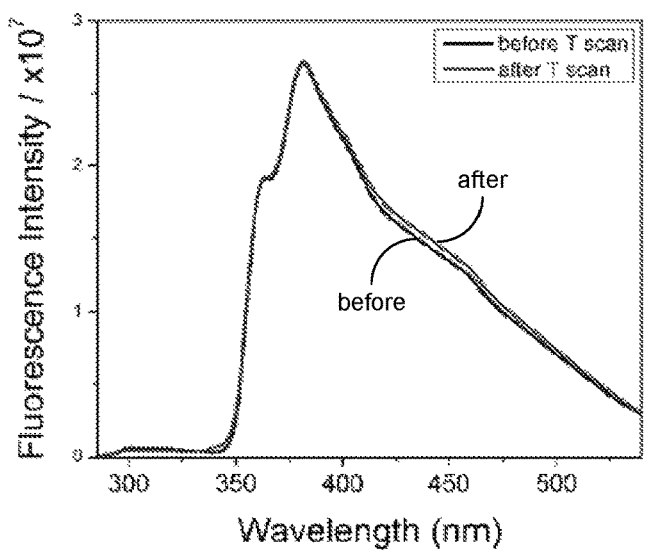

FIGS. 15A through 15C illustrate examples of fluorescence emission spectra and thermal stability of [CI][BETI], in accordance with various embodiments of the present disclosure.

Figure 16A:
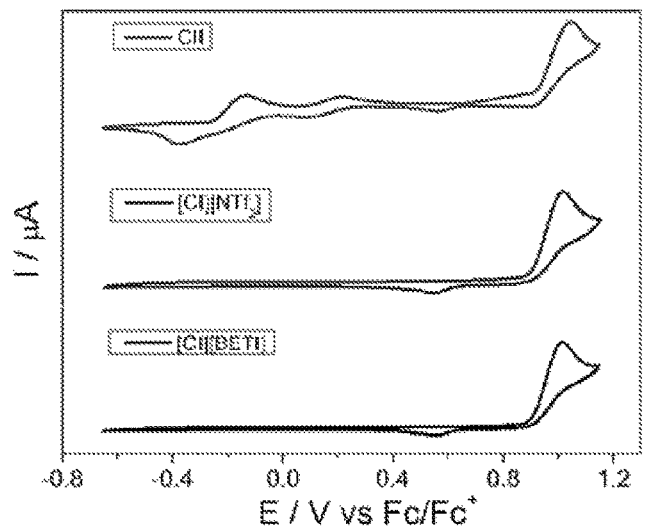

FIG. 16A illustrates examples of cyclic voltammogram results for CII, [CI][NTf$_2$] and [CI][BETI] in DCM, in accordance with various embodiments of the present disclosure.

FIG. 16B is a table illustrating properties of carbazole-based GUMBOS, in accordance with various embodiments of the present disclosure.

FIGS. 17A and 17B are examples of HOMO and LUMO structures for [CI][BETI], in accordance with various embodiments of the present disclosure.

FIG. 18 illustrates examples of synthesized GUMBOS, in accordance with various embodiments of the present disclosure.

FIG. 19A illustrates an example of x-ray diffraction results for [CI][NTf$_2$], in accordance with various embodiments of the present disclosure.

FIG. 19B is a table illustrating physical properties of carbazole-based GUMBOS, in accordance with various embodiments of the present disclosure.

Figure 20:
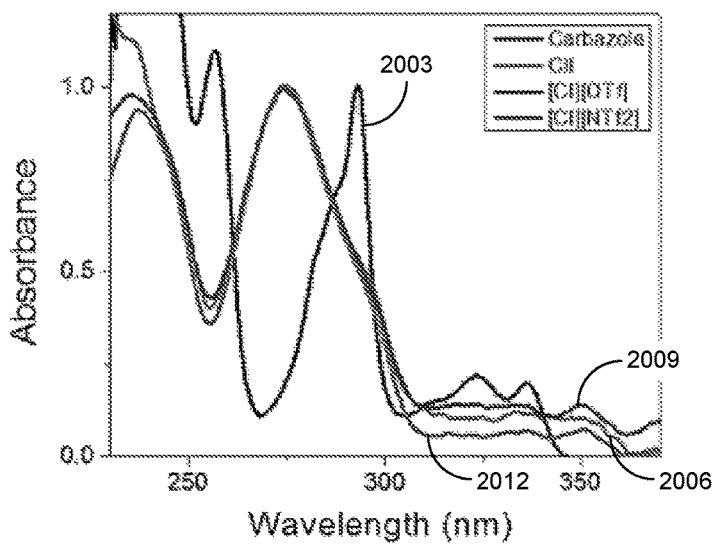

FIG. 20 illustrates an example of normalized absorption spectra of carbazole and carbazole-based GUMBOS in THF, in accordance with various embodiments of the present disclosure.

Figure 21A:
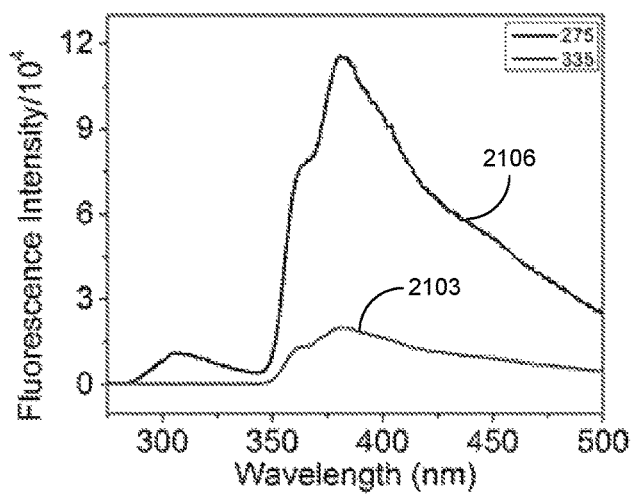
Figure 21B:
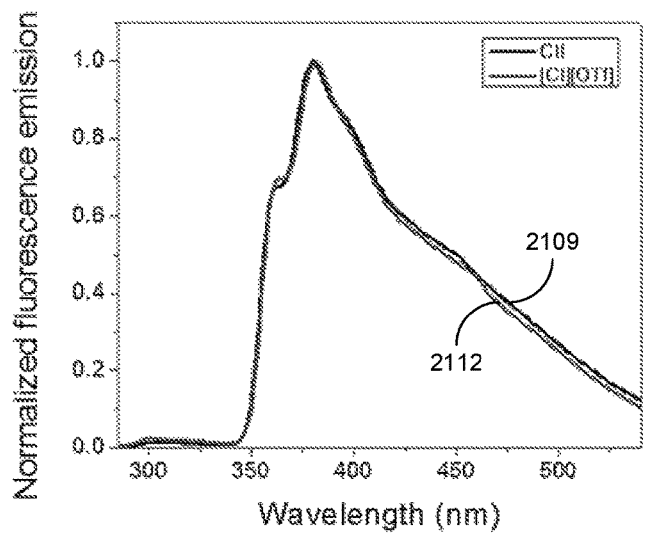

FIGS. 21A and 21B illustrate examples of fluorescence emission spectra of [CI][NTf$_2$] and [CI][OTf] in THF, in accordance with various embodiments of the present disclosure.

FIG. 22 illustrates an example of an excitation-emission spectra of [CI][NTf$_2$] in THF, in accordance with various embodiments of the present disclosure.

FIG. 23 illustrates an example of fluorescence emission and absorption spectra of [CI][NTf$_2$] in THF, in accordance with various embodiments of the present disclosure.

FIG. 24 is a table illustrating examples of fluorescence lifetime data for GUMBOS, in accordance with various embodiments of the present disclosure.

FIGS. 25A and 25B are molecular orbital diagrams representing intramolecular charge transitions in [CI][OTf] and [CI][NTf$_2$], respectively, in accordance with various embodiments of the present disclosure.

Figures 26A, 26B:
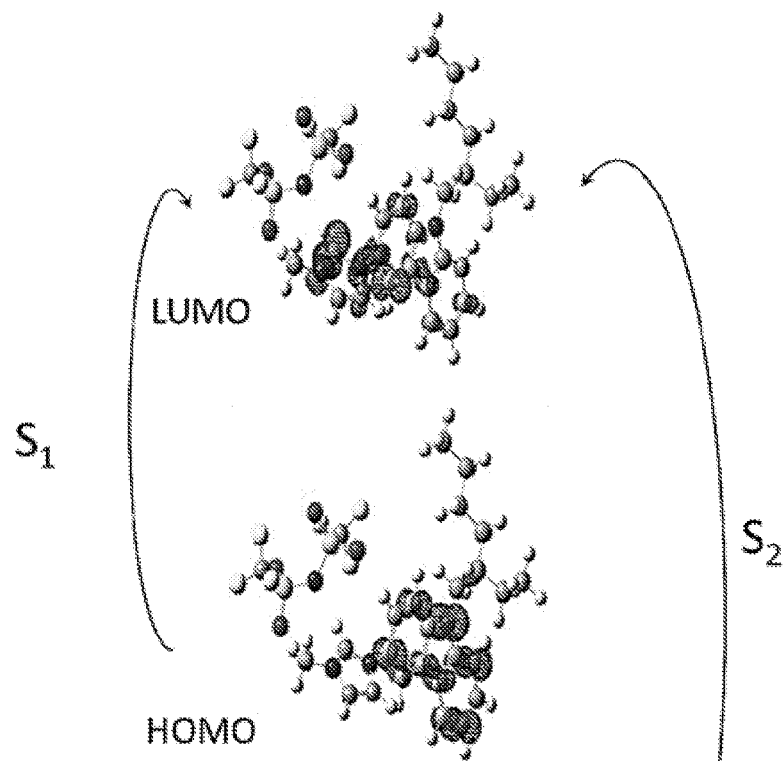

FIG. 26A is a table illustrating calculated band gaps using TDDFT, in accordance with various embodiments of the present disclosure.

FIG. 26B is a molecular orbital diagram representing intramolecular charge transitions in [CI][NTf$_2$], in accordance with various embodiments of the present disclosure.

Figure 27A:
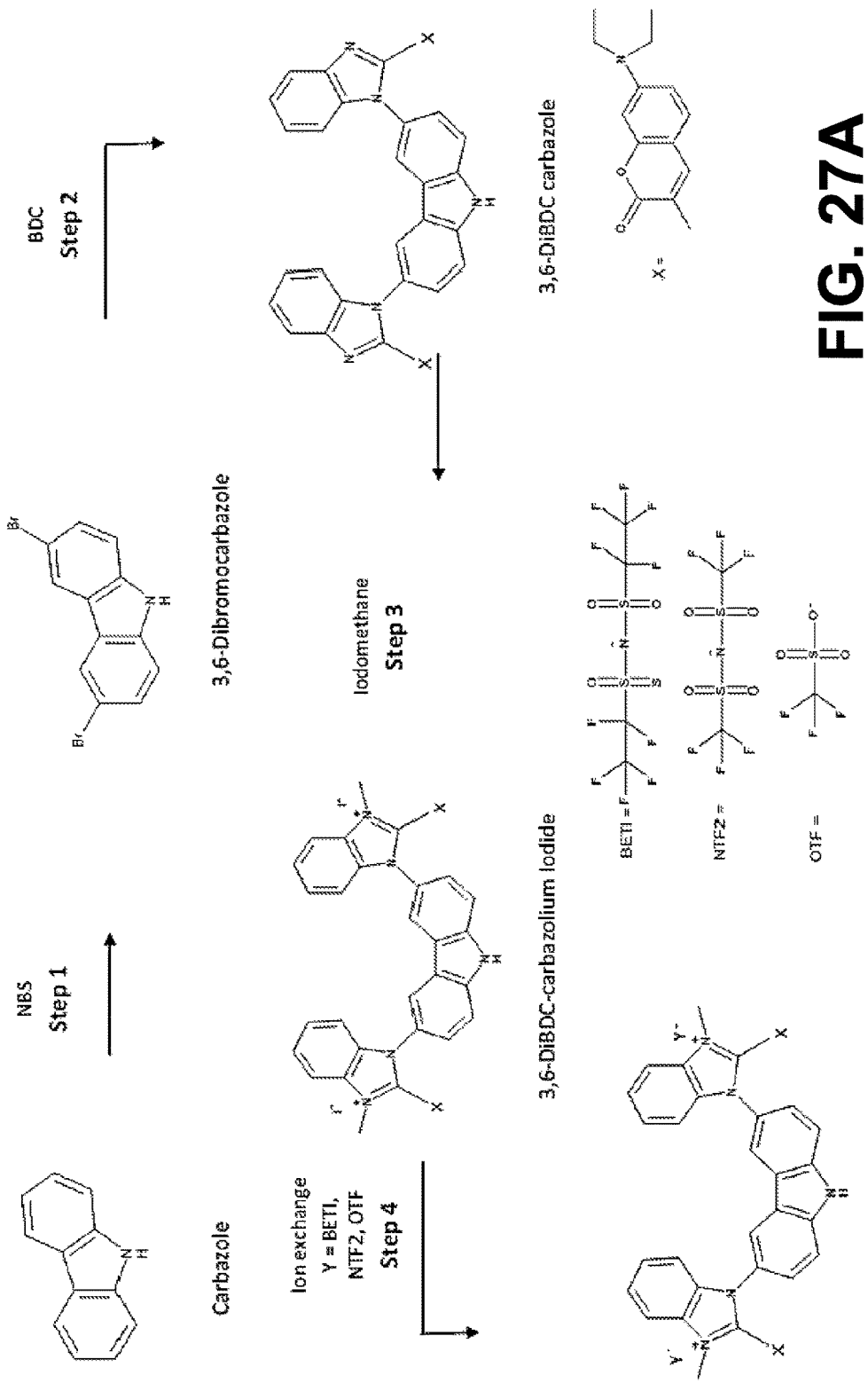
Figure 27B:
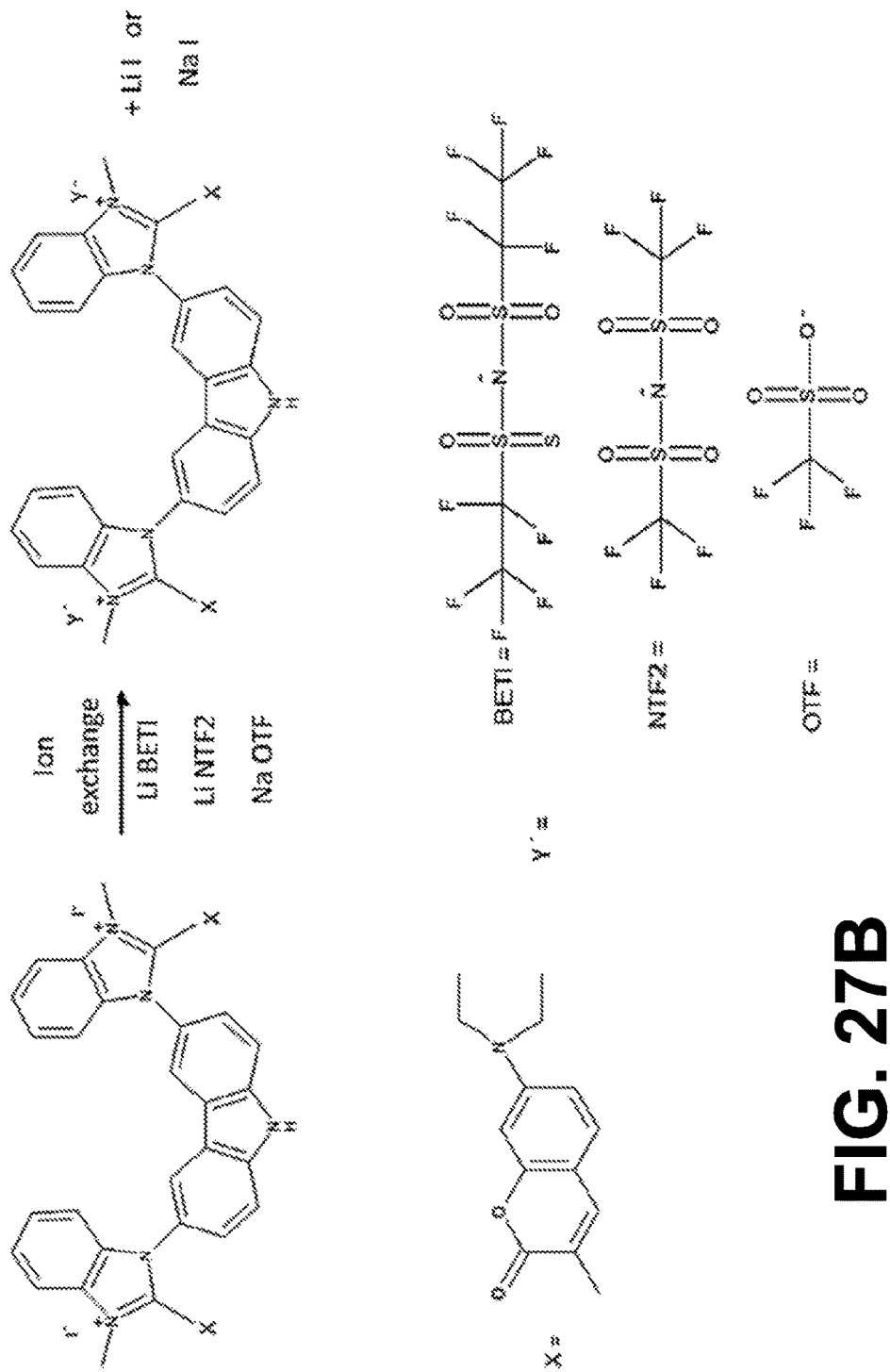

FIGS. 27A and 27B are schematic representations illustrating an example of the synthesis protocol for BDCC-based GUMBOS, in accordance with various embodiments of the present disclosure.

Figure 28A:
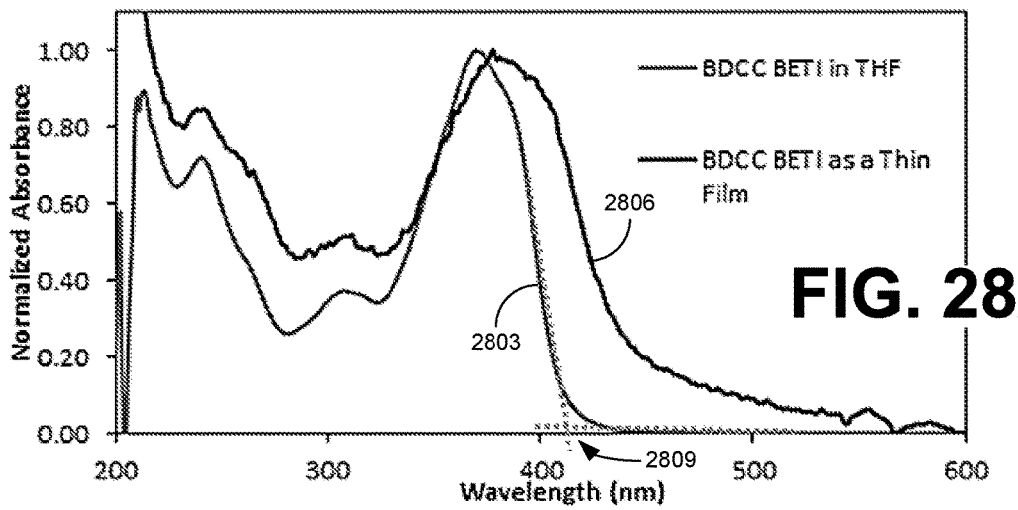
Figure 28B:
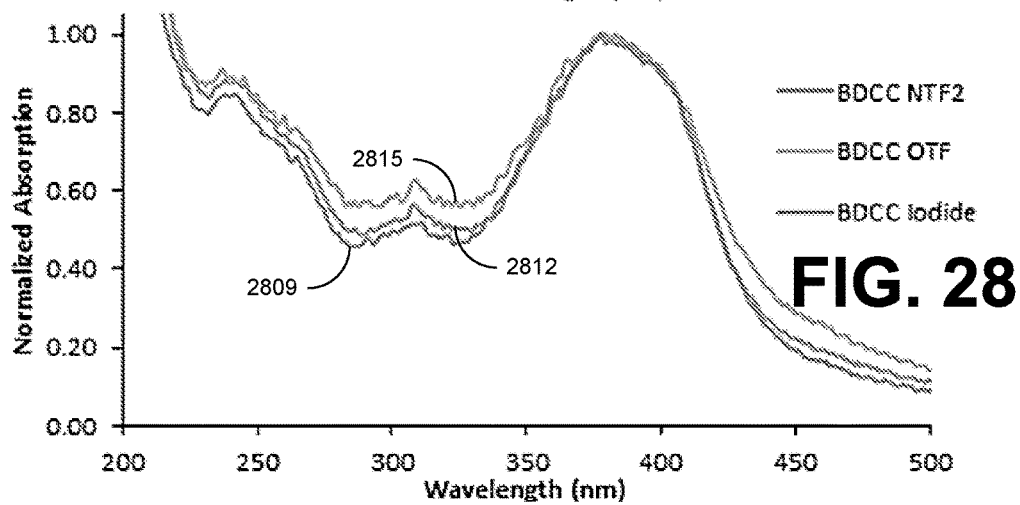
Figure 28C:
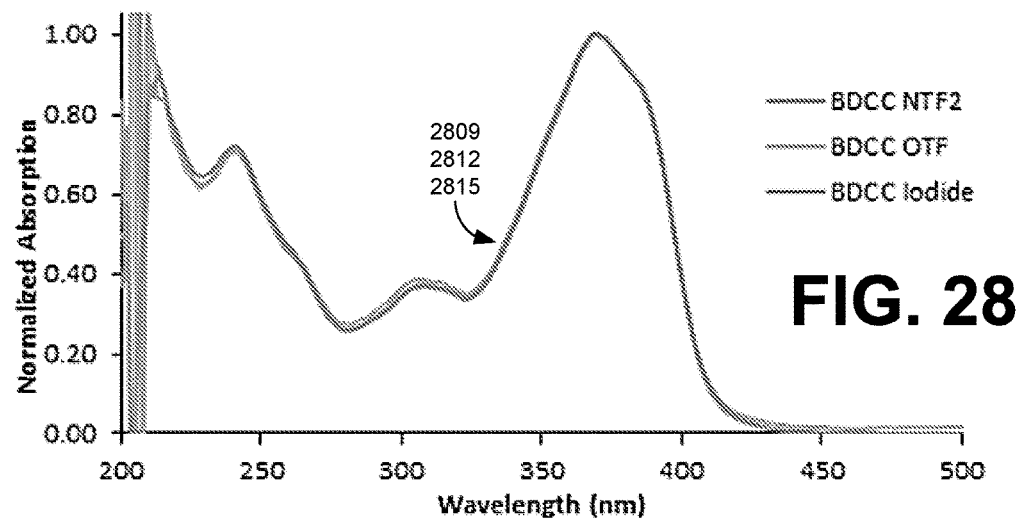

FIGS. 28A through 28C illustrate examples of normalized absorption spectra of BDCC-based GUMBOS in THF and solid films, in accordance with various embodiments of the present disclosure.

Figure 29:
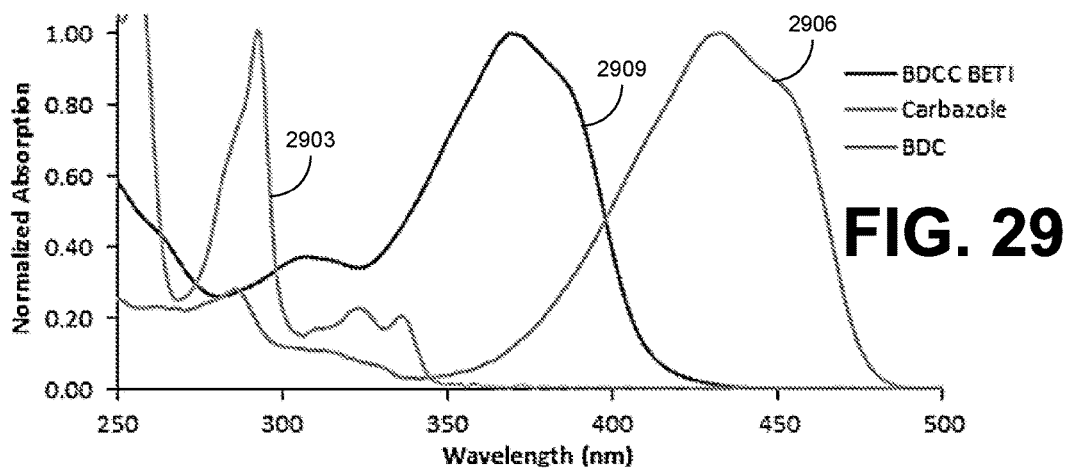

FIG. 29 illustrates an example of normalized absorption spectra of BDCC BETI, carbazole and BDC in THF, in accordance with various embodiments of the present disclosure.

Figure 30A:
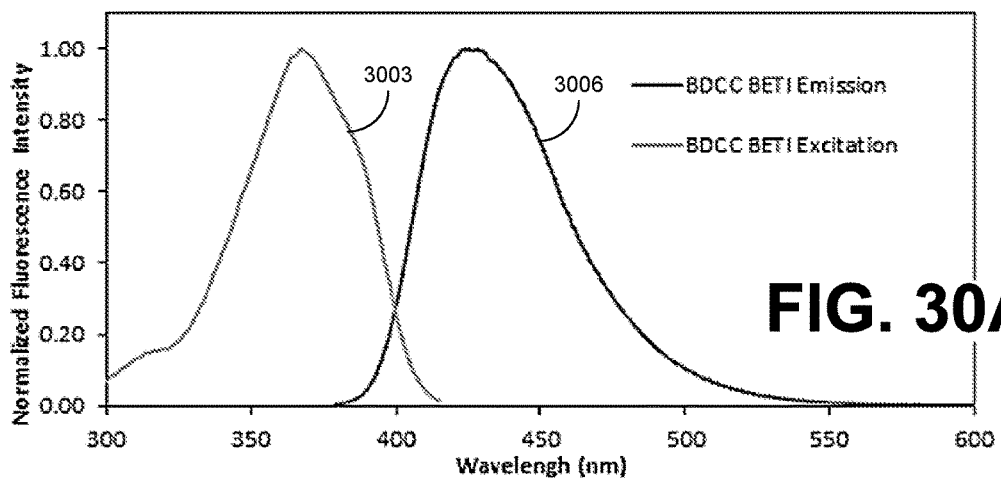
Figure 30B:
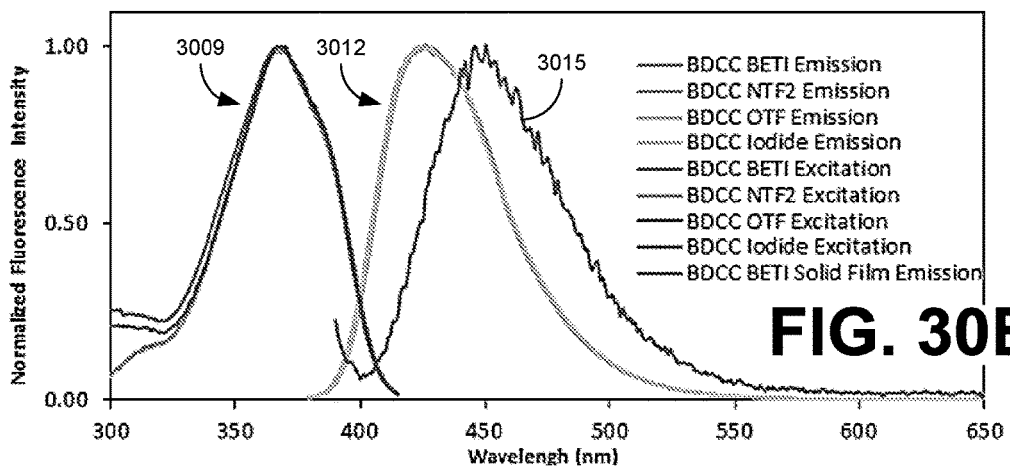

FIGS. 30A and 30B illustrate examples of normalized fluorescence excitation and emission spectra of BDCC-based GUMBOS, in accordance with various embodiments of the present disclosure.

FIG. 31 illustrates an example of normalized fluorescence emission spectra of BDCC BETI, carbazole and BDC in THF, in accordance with various embodiments of the present disclosure.

FIG. 32 is a table illustrating electronic and physical properties of BDCC-based GUMBOS, in accordance with various embodiments of the present disclosure.

Figure 33B:
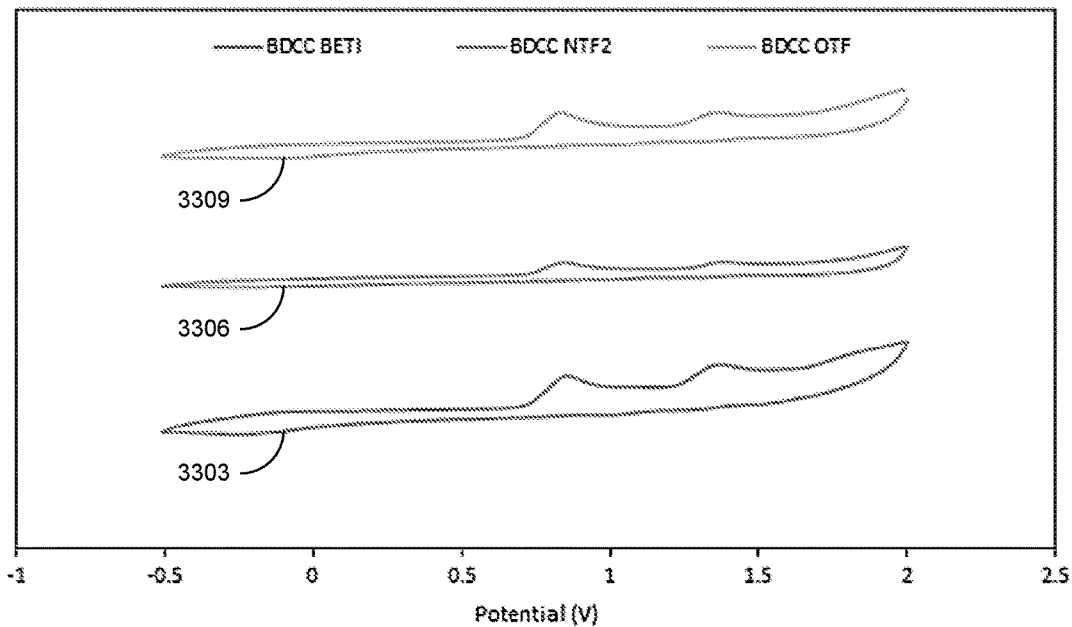

FIGS. 33A and 33B illustrate examples of cyclic voltammogram results for BDCC-based GUMBOS, respectively, in accordance with various embodiments of the present disclosure.

Figure 34:
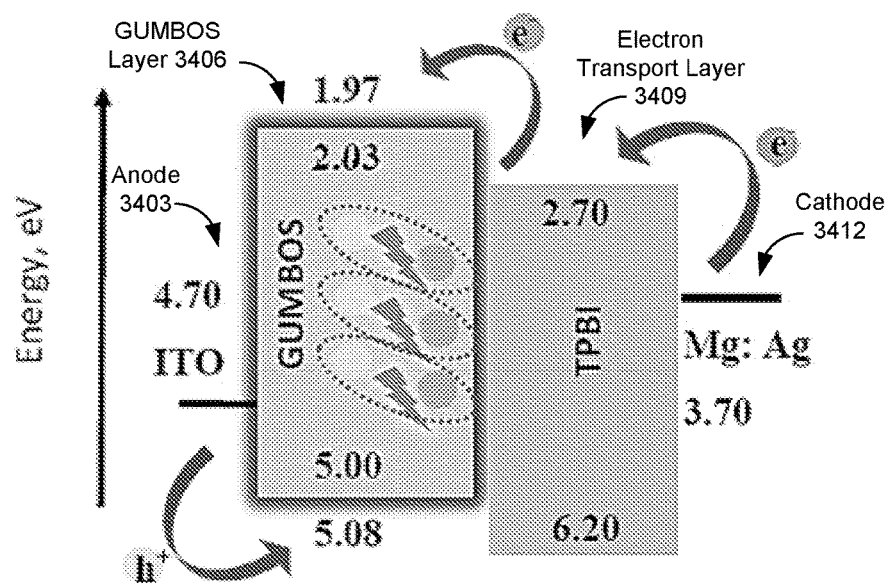

FIG. 34 is a graphical representation of an organic light emitting diode (OLED), in accordance with various embodiments of the present disclosure.

Figure 35:
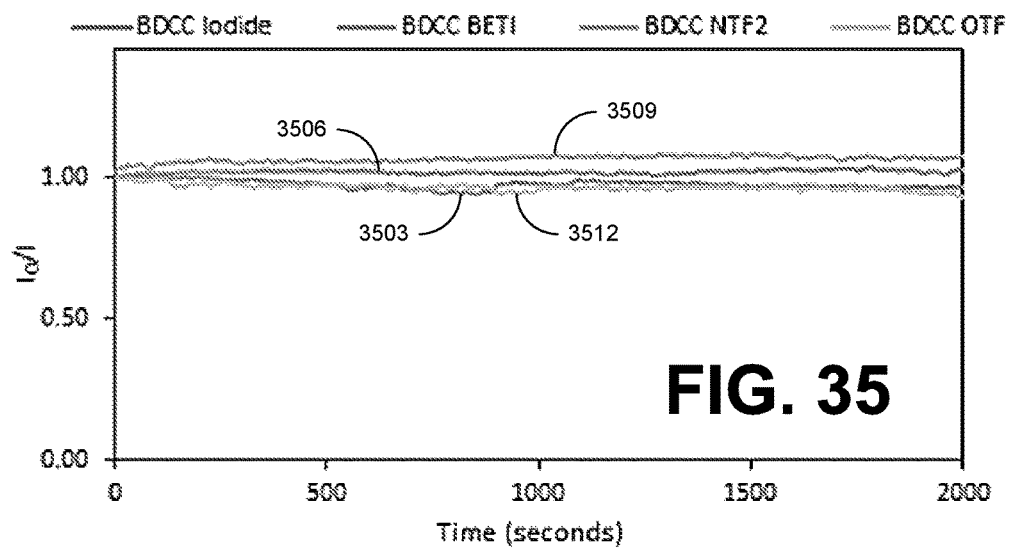
Figure 36:
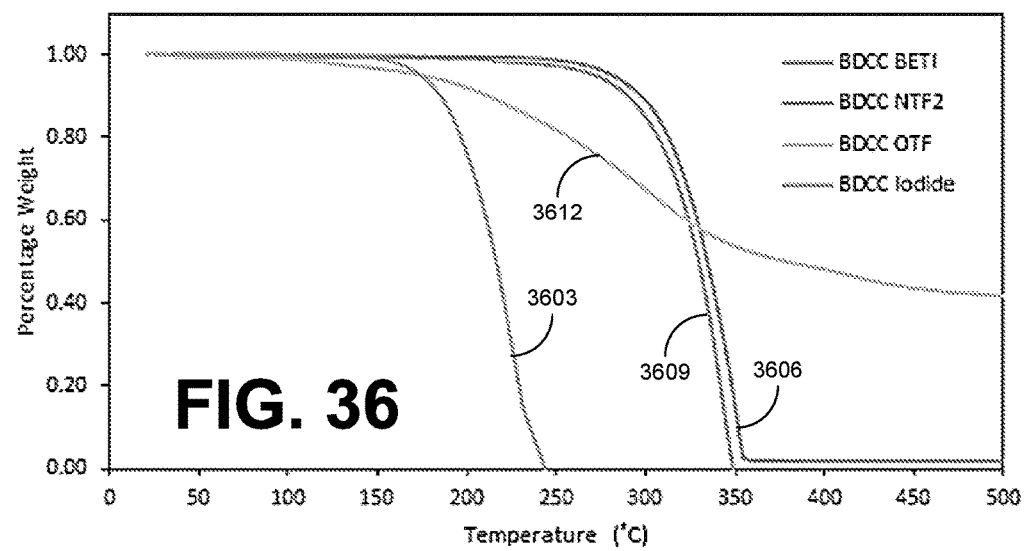

FIGS. 35 and 36 illustrate examples of thermal gravimetric analysis and photo-stability results for BDCC-based GUMBOS, respectively, in accordance with various embodiments of the present disclosure.

Figure 37:
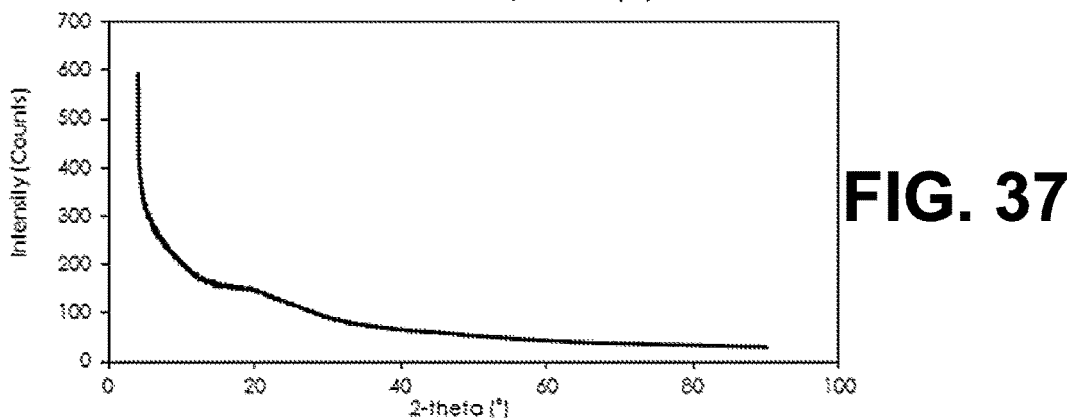

FIG. 37 illustrates an example of x-ray diffraction results for BDCC iodide, in accordance with various embodiments of the present disclosure.

Figure 38:
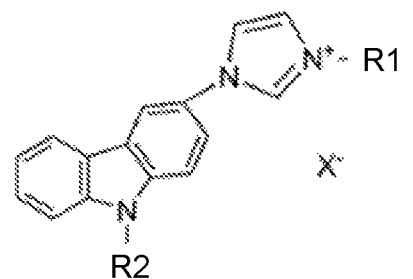
Figure 38:
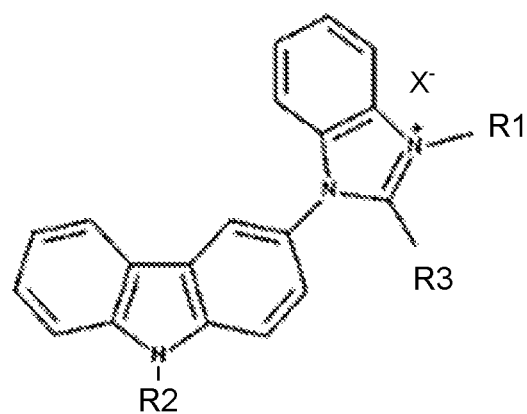
Figure 38:
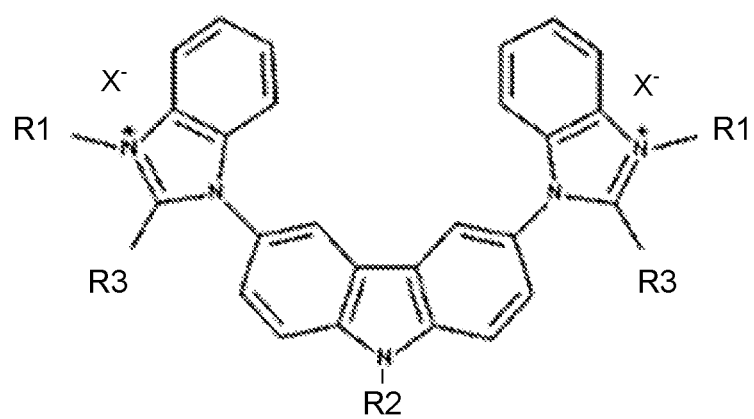

FIG. 38 illustrates examples of the carbazole-based GUMBOS, in accordance with various embodiments of the present disclosure.

DETAILED DESCRIPTION

Disclosed herein are various embodiments related to carbazole-based GUMBOS (group of uniform materials based on organic salts), which can be used in organic light emitting diodes (OLEDs). While ionic liquids are traditionally defined as liquid or low-melting organic salts having melting points less than 100° C., this disclosure examines similar chemistries applied to solid phase organic salts, i.e., GUMBOS with melting points between 25 and 250° C. An embodiment of the carbazole-based GUMBOS is illustrated in FIG. 38. In an embodiment, R1 can be H or an alkyl group (e.g., a C1 to C10, C1 to C6, or C1 to C3 group). In an embodiment, R2 can be H or an alkyl group (e.g., a C1 to C10, C1 to C6, or C1 to C3 group). In an embodiment, R3 can be H, an alkyl group (e.g., a C1 to C10, C1 to C6, or C1 to C3 group), or

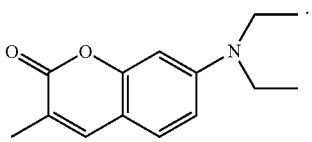 [SMILES: CCN(CC)c1ccc2cc(C)c(=O)oc2c1]

In addition, each H on the carbazole rings can independently be substituted with a halogen. In an embodiment, X⁻ can be a carbazole based counterion. In an embodiment the carbazole based counterion can be an ionic liquid counterion. In an embodiment, when the carbazole-based GUMBOS is a cation, the carbazole-based counterion can include: trifluoromethanesulfonate ([OTf]), bis-(trifluoromethanesulfonyl) imide ([NTf$_2$]), and bis-(pentafluoroethylsulfonyl)imide ([BETI]), tetrafluoroborate (BF4), hexafluorophosphate (PF6), tetraphenylborate (TPB), bis(2-ethylhexyl)sulfosuccinate (AOT), ascorbate (Asc), thiocyanate (SCN), and derivatives of each of these. In another embodiment, when the carbazole-based GUMBOS is an anion, the carbazole-based counterion can include: trihexyl(tetradecyl)phosphonium (P66614), tetraphenylphosphonium (TPP), (4-nitrobenzyl)triphenylphosphonium (4NB), imidazolium (Im), pyridinium (Py), ammonium (NH4), and derivatives of each of these.

Reference will now be made in detail to the description of the embodiments as illustrated in the drawings, wherein like reference numbers indicate like parts throughout the several views. This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the structures disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent. As used herein, "alkyl" or "alkyl group" refers to a branched saturated aliphatic hydrocarbon. Examples of alkyl include, but are not limited to, methyl, ethyl, propyl, iso-propyl, sec-butyl, t-butyl, and iso-pentyl. A lower alkyl refers to an alkyl having 1 to 6 carbons.

Ionic liquid chemistries can be applied in the solid phase to a group of materials with the designation of a group of uniform materials based on organic salts (GUMBOS). Embodiments of the present disclosure provide for compositions including carbazole-based GUMBOS, methods of making carbazole-based GUMBOS, methods of using carbazole-based GUMBOS, and the like. Embodiments of the present disclosure can be used in optoelectronic applications, in particular in organic light emitting diodes (OLEDs). A more detailed description of carbazole-based GUMBOS is provided below in reference to the Examples.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Introduction

The current energy crisis stems from an increase in energy consumption, as well as depletion in energy resources. In this regard, developments in optoelectronic devices based on organic semiconducting and photo-emissive materials can expand the horizons of optoelectronics. In addition to significantly lower energy consumption, organic optoelectronics have distinct advantages over conventional inorganic optoelectronics such as reduced cost, lower weight, eco-friendliness, flexibility, less engineering restrictions for designing actual electronic devices, and high efficiency.

A class of organic salt materials known as GUMBOS, which are solid phase organic salts with melting points lower than 250° C., is presented in this disclosure. The ability to select the anion, cation or both to tune the polarity of entire molecules along with other tunable chemical, physical, spectral, and electronic properties allow GUMBOS to be tailor-made for specific tasks. GUMBOS type compounds have been successfully applied to many fields including but not limited to medicine, biochemistry and microbiology, sensing, separation science, and nano-technology, Utilization of GUMBOS in the field of optoelectronics by synthesizing imidazolium substituted carbazole-based GUMBOS are disclosed for OLED applications.

Devices containing organic semiconducting materials which can produce, detect, and control light are considered organic optoelectronics. In this disclosure, the focus is on applications such as those in the field of OLEDs. OLEDs are heavily exploited in color displays and other lighting purposes with a continually growing market. OLEDs are defined as solid state semiconducting diodes produced by applying a thin film of electroluminescent organic material, i.e., a material that produces light as the output when the input is electricity. Electricity causes the emissive layer to release photons as a result of a combination of 'holes' in the valence band and electrons in the conduction band of the organic semiconductor. The color of the emitted light depends on the HOMO and LUMO band gap of the organic semiconductor. Red, green and blue light emitting materials are important for full color displays.

OLEDs have distinct advantages over conventional inorganic LEDs, liquid crystal displays (LCDs) and plasma displays as OLEDs have low power consumption, rapid response time, wide color gamut, better contrast, better viewing angles, light weight, flexibility, and transparency. However, many OLED semiconducting materials have limited photo and thermal stability which leads to degeneration of emissive organic materials rapidly over time. The performance and longevity of OLED based electronic device can be severely affected by this emissive layer degeneration. In general, blue OLED emitters are more susceptible to degradation. As a result, green and red OLEDs have longer lifetimes with half lifetime ($LT_{50}$) ranging, e.g., from 200,000 to 400,000 hours and from 250,000 to 900,000 hours, respectively, while blue OLEDs continue to suffer from shorter lifetimes (e.g., $LT_{50}$ less than 20,000) and difficulty in fabrication. In addition, it has been observed that it is quite difficult to extend the lifetime of pure dark blue fluorescence organic emitters to more than 10,000 hours. Thus, there is an advantage to have stable and efficient blue OLED materials. Improvements for blue OLEDs can include phosphorescence organic light emitting diodes (PHOLEDs), polymer light emitting diodes (PLEDs), and quantum cutters. This disclosure presents the development of highly efficient blue fluorescence semiconductor materials for the rapidly growing OLED market.

Example 1

In this study, synthesis and characterization of carbazole-based group of uniform materials based on organic salts (GUMBOS), as well as potential applications of these compounds, is reported. These organic-based compounds exhibit high thermal stability (decomposition temperatures in the range of about 350° C. to about 500° C.) and photostability. In addition, these compounds have appreciably high fluorescence quantum yields (e.g., 73-99%) with broad emissions in the visible region and quantum yields which depend on the GUMBOS counteranion. This quantum yield was observed in DCM solvent; however, quantum yields of unity (100%) can be readily achieved. The physicochemical, optical, and electrochemical properties of these materials were investigated and are detailed here. Evaluation of band gap values (e.g., 3.4 eV), HOMO-LUMO energy levels, and measured fluorescence quantum yields as compared to carbazole suggest the potential use in organic light-emitting diodes. Computational results were found to be complementary to experimental results, and calculated band gaps were in agreement with experimentally obtained values.

A class of solid phase materials designated by the acronym GUMBOS (group of uniform materials based on organic salts) is examined. GUMBOS, which are solid state versions of ILs, exhibit a broad range of melting points (25-250° C.). In addition to retaining the most interesting properties of ILs such as tunability, high thermal stability, and nonflammability, GUMBOS have been shown to have multifaceted applications including biomedical imaging, photovoltaics, and antimicrobial agents, as well as other applications. In the present disclosure, the synthesis of novel organic semiconductor-based GUMBOS that exhibit desired characteristics for use in organic light emitting diodes (OLEDs) and other optoelectronic applications is reported.

Carbazole derivatives have been widely exploited for their electronic and optical properties and are extensively used in optoelectronic devices. These applications can be realized as a result of their semiconductor properties, transporting ability, and great thermal characteristics. In this regard, many different derivatives with extended conjugation as well as polymer components can be synthesized to incorporate the amorphous characteristics with high thermal stability needed for OLEDs applications. Examination of the literature indicates that several bulky carbazole-based molecules have been reported with increased conjugation achieved via long synthetic approaches, ultimately leading to rather expensive compounds. Moreover, many of these synthetic procedures are quite complicated and tedious, including a number of steps which result in low yields.

In regard to organic-based OLEDs, a relatively small molecule for this use has been reported by "Organic Electroluminescent Diodes" by C. W. Tang and S. A. VanSlyke (*Appl. Phys. Lett.* 1987, 51, 913-915), which is hereby incorporated by reference in its entirety. Small organic-based compounds can be efficiently used as optoelectronic materials. Note that modest increases can be achieved in OLEDs efficiency by use of imidazolium ionic liquids, which can enhance charge transport as well as improve the efficiency of OLEDs. These characteristics of carbazole and the significant contributions of ionic liquids to optoelectronics are examined here. The present study examines the synthesis of a low-cost, highly efficient fluorescent material that can be used in OLEDs. In this regard, a carbazole-based GUMBOS was prepared by introduction of an imidazolium ring onto the third carbon of the carbazole unit and use of iodide as the counteranion. An ionic conductor, carbazoleimidazoleiodide solid electrolyte, has also been synthesized as a triiodide transportation material for use in solid state dye-sensitized solar cells (DSSCs) in "A New Class of Solid State Ionic Conductors for Application in All Solid State Dye Sensitized Solar Cells" by Midya et al. (*Chemical Communications,* 2010, 46, 2091-2093), which is hereby incorporated by reference in its entirety.

A similar synthetic procedure was adopted for the present study. In this regard, synthesis of a derivative of carbazole-based GUMBOS via simple attachment of various groups at the 3-, 6-, and/or N-position of carbazole can be implemented. Derivatives of the carbazole-based GUMBOS can be synthesized using a carbazole-based counterion. In an embodiment, the carbazole-based counterion can be a counterion used in ionic liquids. In an embodiment, when the carbazole-based GUMBOS is a cation, the carbazole-based counterion can include: trifluoromethanesulfonate ([OTf]), bis-(trifluoromethanesulfonyl)imide ([$NTf_2$]), and bis-(pentafluoroethylsulfonyl)imide ([BETI]), tetrafluoroborate (BF4), hexafluorophosphate (PF6), tetraphenylborate (TPB), bis(2-ethylhexyl)sulfosuccinate (AOT), ascorbate (Asc), thiocyanate (SCN), and derivatives of each of these. In another embodiment, when the carbazole-based GUMBOS is an anion, the carbazole-based counterion can include: trihexyl(tetradecyl)phosphonium (P66614), tetraphenylphosphonium (TPP), (4-nitrobenzyl)triphenylphosphonium (4NB), imidazolium (Im), pyridinium (Py), ammonium (NH4), and derivatives of each of these. This approach was adapted for the current synthesis to obtain carbazoleimidazole-based GUMBOS with preferred characteristics such as amorphous morphologies, appropriate redox potentials, high fluorescence quantum yields in the visible (particularly blue) region, and great thermal and photostability. Three different derivatives of the carbazoleimidazole-based cation were synthesized using trifluoromethanesulfonate ([OTf]), bis-(trifluoromethanesulfonyl)imide ([NTf$_2$]), and bis-(pentafluoroethylsulfonyl)imide ([BETI]) as the counteranions. These three anions were chosen to investigate their effects on the physicochemical properties of the parent compound as a result of increasing trifluoromethane chain with increasing hydrophobicity.

The counterions [NTf$_2$] and [BETI] can impart higher thermal and photostabilities. The present study was designed to employ simple synthesis of carbazoleimidazole-based GUMBOS. Such GUMBOS can provide broad fluorescence emission due to extensive conjugation between the carbazole and the imidazole unit, with good quantum yields, suitable band gaps, high thermal and photostability, and excellent prospects for applications in optoelectronics. Bulky carbazole derivatives can be employed as hole transport materials as well as emissive materials in OLEDs owing to their excellent hole transporting properties and high thermal, morphological, and photostability. Materials can be synthesized which emit at low wavelengths in order to develop a white light source by incorporating other colored materials. However, it is not easy to obtain a material with blue emission for OLEDs fabrication due to several previously reported problems.

The carbazole-based GUMBOS described in this study, exhibit characteristics such as amorphous properties, thermal stabilities, appropriate band gap values, strong broad fluorescence emission, and unexpectedly high quantum yields with appreciably good photostabililties. All these properties together constitute an appropriate combination for their potential applicability in OLEDs as blue-emitting or hole transport materials.

Experimental Method

Materials.

Carbazole, N-bromosuccinimide, sodium hydride, 2-ethylhexyl bromide, 1,10-phenanthroline, sodium sulfate, sodium trifluoromethanesulfonate (NaOTf), lithium bis(trifluoromethylsulfonyl)imide (LiNTf$_2$), lithium bis-(pentafluoroethylsulfonyl)imide (LiBETI), iodomethane, and dimethylformamide were purchased from Sigma Aldrich and used as received. Imidazole was purchased from Fluke. Hexane and methanol (MeOH) were purchased from OmniSolv, dicholoromethane (DCM) was from J. T Baker, and diethyl ether was purchased from Fisher Scientific. Triply deionized water (18.2 MΩ cm) was obtained by use of an Elga model PURELAB ultra water-filtration system and was used for all ion exchange reactions.

Instrumentation.

The thermal decomposition temperature of each compound was measured by use of a Hi Res Modulated TGA 2950 Thermogravimetric Analyzer TA Instrument. Absorbance measurements were performed using a Shimadzu UV-3101PC and a UV-vis-near-IR scanning spectrometer (Shimadzu, Columbia, Md.). Fluorescence studies were performed using a Fluorolog-3 spectrofluorimeter (model FL3-22TAU3; HORIBA Scientific, Edison, N.J.). A 0.4 cm path length quartz cuvette (Starna Cells) was used to collect fluorescence and absorbance against an identical cell filled with solvent as the blank. Fluorescence studies were all performed using right angle geometry. Quantum yields were measured using an integrated sphere, and measurements of quantum yields were conducted on a HORIBA Scientific Quanta φ accessory (150 mm diameter) coupled with Spex Fluorolog-3 spectrofluorimeter (model FL3-22TAU3; HORIBA Scientific, Edison, N.J.). Quantum yields were measured using a stoppered quartz cuvette of 1 cm path length (Starna Cells).

Fluorescence lifetimes were measured on a FluoroCube, spectrofluorimeter (model FluoroCube, HORIBA Scientific, Edison, N.J.) using the time domain mode. A picosecond pulsed LED excitation source of 273 nm was used and emission collected at 385 nm in MeOH and at 440 nm in DCM with a TBX detector. The time-correlated single photon counting (TSCPC) mode was used for data acquisition with a resolution of 7 ps/Channel.

Quartz glass was purchased from SPI supplies and used to prepare solid films. Solid films were prepared using Gamma High Voltage Research, Inc., coupled with a Harvard apparatus to simultaneously control the voltage and flow rate. Films were characterized by use of scanning electron microscopy (SEM) and fluorescence microscopy. The photostabilities of GUMBOS containing hydrophobic anions were studied over a period of 3000 s at 275 nm with emission and excitation slit widths of 14 nm. Temperature-dependent fluorescence studies were also performed over the temperature range of 20-60° C. with 5° intervals to investigate temperature-dependent changes in fluorescence, as well as reversibility of these properties upon cooling.

Cyclic voltammetric measurements were performed using an Autolab/EAs 2 computer-controlled electrochemical system equipped with a potentiostat (model PGSTAT 302N) and GPES (version 4.9.007) software. Cyclic voltammograms (CVs) of these three compounds were recorded separately by using Pt as a working and counter electrode. The working electrode was polished using wet filter paper prior to any experiments. The reference electrode was Ag/AgCl, while ferrocene was used as an internal reference electrode. The supporting electrolyte was 0.1 M tetrabutylammonium hexafluorophosphate (TBAPF$_6$) prepared in an organic solvent (DCM). The potential window was determined by running the CV of the supporting electrolyte solution followed by performance of cyclic voltammetry on the GUMBOS and ferrocene. These measurements were performed at different scan rates. Cyclic voltammograms were analyzed to determine peak potentials, which were later used to calculate band gaps.

Computational Details. The Gaussian 09 program was utilized for calculations in the present study. The geometric structures of compounds were visualized using GaussView 5.0. The ground state geometries of GUMBOS including both counterions were first optimized using density function theory (DFT) and post-optimized using time-dependent density function theory (TDDFT) to calculate the transition energies. The hybrid DFT Becke's three-parameter nonlocal exchange functional, with a correlation function similar to Lee-Yang-Parr31 (B3LYP), was used for all calculations. A diffuse function basis set of 6-31+G(d,p) was employed. The choice of basis set with polarized (for heavy and hydrogen atoms) and diffuse functions was made for a better description of electrons relatively far from the nucleus as well as success of B3LYP/6-31+G(d,p) in a similar study. Vibrational frequencies were analyzed in order to confirm the optimized structures as a local minima. Optimized structures were used for TDDFT using the same model chemistry (B3LYP/6-31+G(d,p)).

Synthesis and Characterization

Carbazoleimidazolium iodide (CII) was synthesized following a protocol described in the literature. Details of this procedure are presented in the Supporting Information section below. Various derivatives were prepared by use of a simple anion exchange method. Iodide ion from CII was replaced with organic hydrophobic anions through a simple anion exchange procedure. This reaction was performed in a biphasic solution, where CII was dissolved in dichloromethane (DCM) and highly concentrated solutions of other salts were prepared using deionized (DI) water. Carbazoleimidazolium trifluoromethanesulfonate [CI][OTf] was prepared by using the corresponding sodium salt, whereas carbazoleimidazolium bis-(trifluoromethylsulfonyl)imide [CI][NTf$_2$] and carbazoleimidazolium bis(pentafluoroethylsulfonyl)imide [CI][BETI] were synthesized by use of their lithium salts. After stirring for 3-4 days, the lower layer of DCM was separated from water, and later the DCM layer was washed with water several times to remove the byproduct (lithium or sodium salt of iodide) which is highly soluble in water. DCM was evaporated under high vacuum and freeze-dried to remove small amounts of water. These compounds were characterized by use of ESI-MS, H NMR, and 19F-NMR.

Exemplary synthesis schemes and structures of the cation and anions are shown in FIGS. 1A and 1B. While FIGS. 1A and 1B show an imidazole group at a third carbon position of the carbazole unit, the imidazole group can also be positioned on the 6 or N-position of the carbazole unit as well (e.g., the imidazole group can be located on the 3, 6, and/or N-position) (see FIG. 38 for exemplary carbazole-based GUMBOS). In addition, a methyl imidazole group is shown in FIGS. 1A and 1B, but the methyl imidazole group can also be an alkyl imidazole group or imidazole in other embodiments, where the alkyl group can be a C1 to C6 hydrocarbon group or a C1 to C3 hydrocarbon group. Furthermore, the $C_8H_{17}$ group shown in FIGS. 1A and 1B can be substituted with hydrogen or an alkyl group, where the alkyl group can be a C1 to C10 hydrocarbon group, C1 to C6 hydrocarbon group, or a C1 to C3 hydrocarbon group. In an embodiment, the methyl group and/or the $C_8H_{17}$ group shown in FIGS. 1A and 1B can each be independently selected from hydrogen or an alkyl group, where the alkyl group can be a C1 to C10 hydrocarbon group, C1 to C6 hydrocarbon group, or a C1 to C3 hydrocarbon group. In addition, each of the hydrogen groups on the carbazole rings can independently be optionally substituted with, e.g., a halogen.

Thermal Gravimetric Analysis (TGA). Samples were heated gradually from room temperature to 600° C. at a rate of 10° C. min$^{-1}$. Values of the onset temperature were determined using TA universal analysis software, and these values were reported as the decomposition temperature ($T_d$). Examination of TGA data indicated that these carbazole-based salts possessed good thermal stability, with decomposition temperatures ($T_d$) ranging from 395 to 500° C. The results obtained for various anions with the same carbazoleimidazolium cation showed that thermal stability was greatly enhanced with [BETI], [NTf$_2$], or [OTf], as compared to the iodide-based parent compound. These results clearly demonstrated that the $T_d$ was primarily dependent on the anion, with hydrophobic anions exhibiting high thermal stability as depicted in the table of FIG. 2.

Figure 3A:
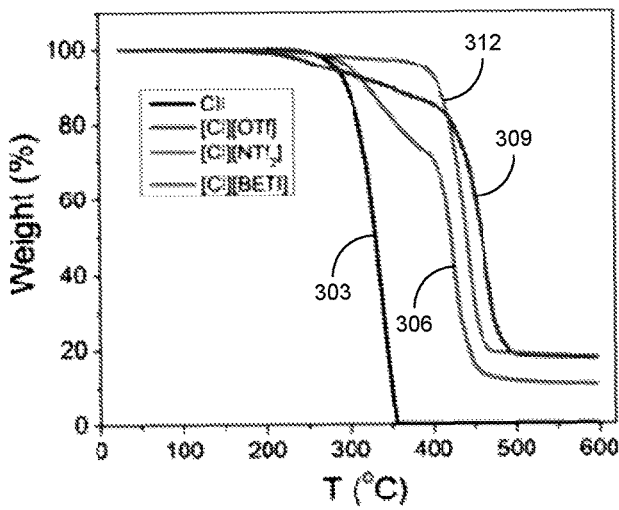
FIGS. 3A and 3B illustrate examples of thermal gravimetric analysis results for CII, [CI][OTf], [CI][NTf$_2$], [CI][BETI], NaOTf and LiNTf$_2$, in accordance with various embodiments of the present disclosure.
Figure 3B:
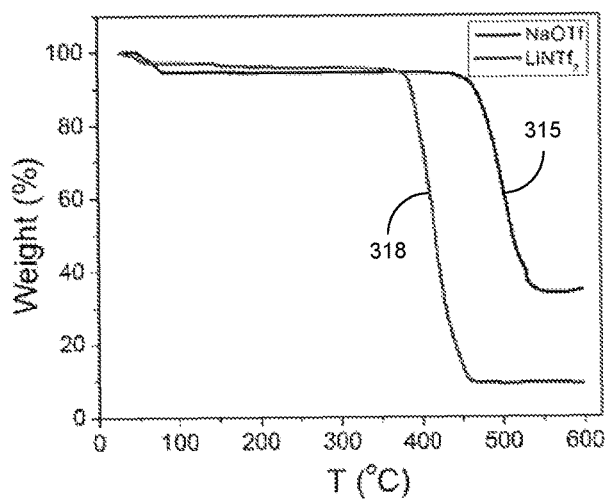

The final decomposition temperature of GUMBOS containing [BETI] and [NTf$_2$] anions were comparable. These results were consistent with previous studies, where [NTf$_2$] and [BETI] counteranions exhibited higher and comparable thermal stabilities. [CI][ NTf$_2$] and [CI][OTf] showed respectively almost 17% and 30% of weight loss before reaching the final decomposition temperature. The remaining residue of about 11-17% may be attributed to the anions. TGA plots are shown in FIG. 3A of CII (curve 303), [CI][OTf] (curve 306), [CI][NTf$_2$] (curve 309), and [CI][BETI] (curve 312), and the data obtained from the onset are tabulated in the table of FIG. 2. FIG. 3B illustrates the TGA for NaOTf (curve 315) and LiNTf$_2$ (curve 318).

Results

X-Ray Diffraction (XRD).

Figure 4:
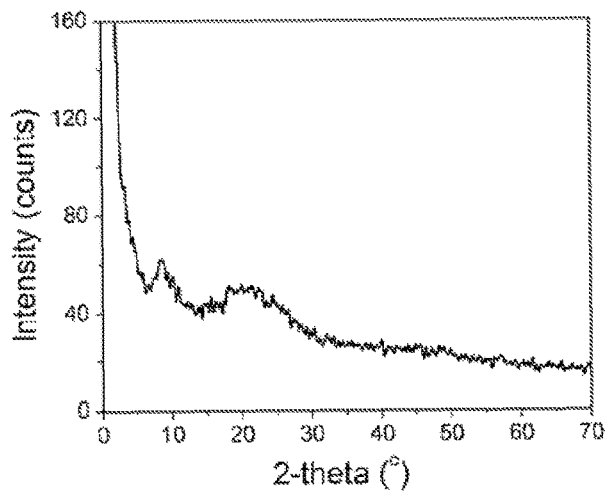
FIG. 4 illustrates an example of x-ray diffraction results for [CI][NTf$_2$], in accordance with various embodiments of the present disclosure.

X-ray diffraction was used to estimate the morphology of the GUMBOS. Extensive research was performed to design amorphous materials to avoid nonlinear optical activity from the crystalline materials. Molecules that exhibit packing difficulty show stable amorphous characteristics with high morphological stability. Thus, the materials derived in this study should be amorphous due to frustrated packing in GUMBOS produced by use of bulky cations. Examination of XRD data for [CI][NTF$_2$] showed a broad indistinguishable peak in the XRD spectrum which reveals the amorphous properties of these GUMBOS as depicted in FIG. 4. The amorphous properties of these GUMBOS may be attributed to the presence of an ethylhexyl chain on the nitrogen of carbazole which decreases the chances of constricted packing of ions.

UV-Vis Spectroscopy.

Figure 5A:
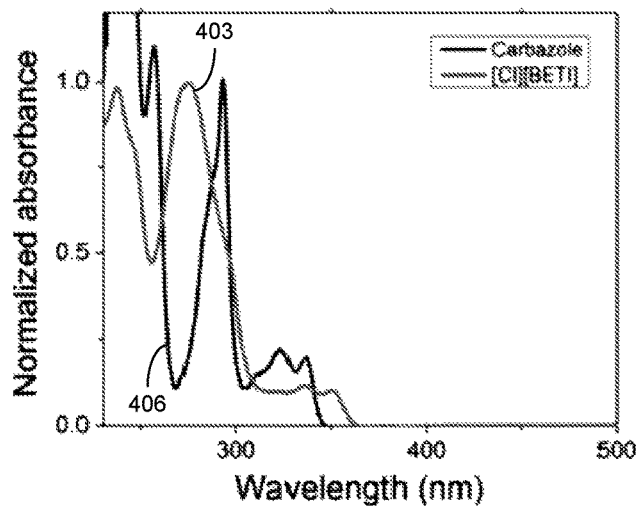
FIGS. 5A through 5C illustrate examples of normalized absorption spectra of [CI][OTf], [CI][NTf$_2$] and [CI][BETI], in accordance with various embodiments of the present disclosure.
Figure 5B:
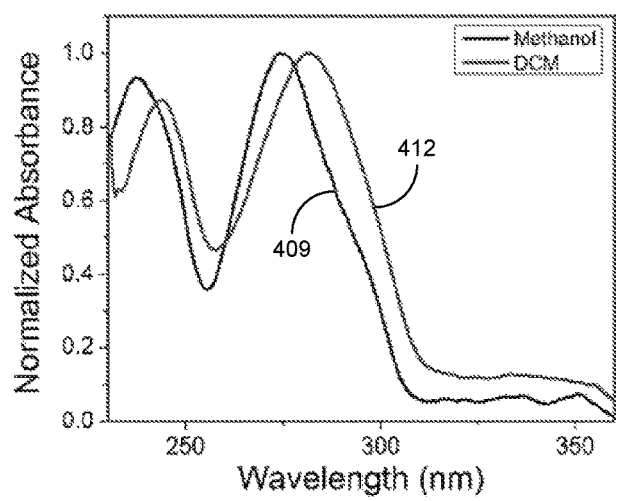
Figure 5C:
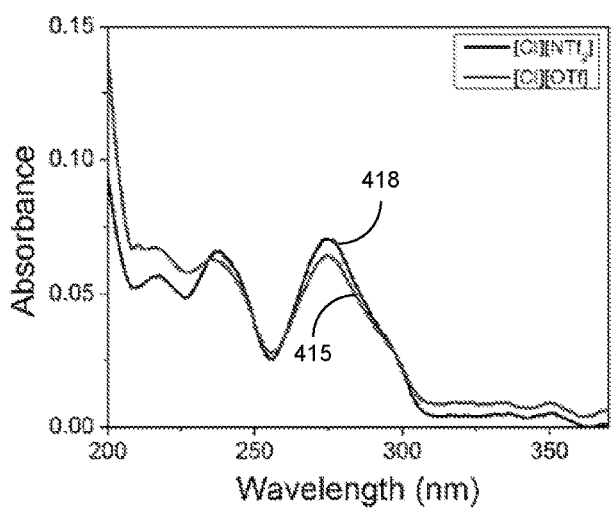

Absorption spectra of all GUMBOS were recorded and are shown in FIGS. 5A-5C. Solutions were prepared in methanol, DCM, and THF. FIG. 5A illustrates the normalized absorption spectra of [CI][BETI] (curve 403) and carbazole in methanol (curve 406). The absorption spectrum of [CI][BETI] exhibited two highly intense peaks at 236 and 275 nm as well as two lower intensity bands at 335 and 350 nm. The peaks at 335 and 275 nm may be attributed to first ($S_1$) and second singlet ($S_2$) excited states, respectively, as represented in the literature for carbazole and its different derivatives. As shown in FIG. 5A, formation of [CI][BETI] led to a peak shift from 290 nm (for pure carbazole) to 275 nm which is possibly due to the presence of quaternary nitrogen in the ring. The red shift of the first singlet excited state peak from 322 to 335 nm was observed in carbazole-based GUMBOS, as compared to carbazole. This shift may be attributed to the extensive conjugated system. Thus, there was a significant increase in the energy gap between $S_1$ and $S_2$ in the GUMBOS compounds. All absorption peaks may be attributed to the carbazoleimidazolium cation (FIG. 5A), and as expected, none were contributed by the anion. FIG. 5B illustrates the normalized absorption spectra of [CI][NTf$_2$] in methanol (curve 409) and DCM (curve 412). A very small shift of 5 nm was observed for a compound in two different solvents as depicted in FIG. 5B. FIG. 5C illustrates the absorption spectra of [CI][OTf] (curve 415) and [CI][NTf$_2$] (curve 418) in methanol. As expected, no peak shifts were observed for the carbazoleimidazolium cation when conjugated with different anions in a given solvent as shown in FIG. 5C.

Figure 6:
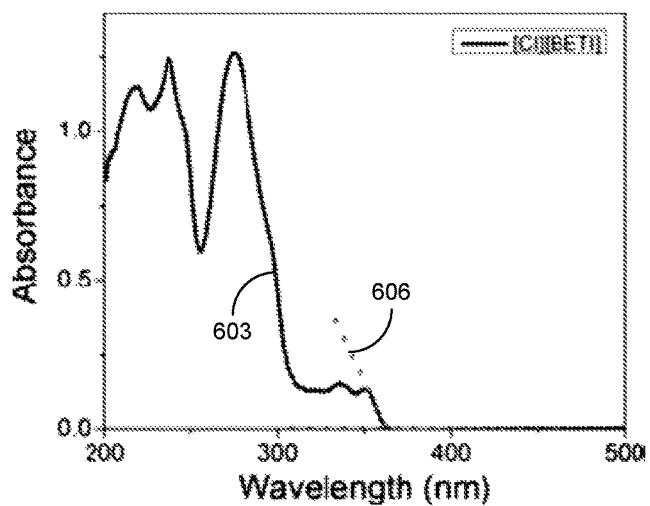
FIG. 6 illustrates an example of an absorption spectrum of [CI][BETI] in DCM to show onset wavelength, in accordance with various embodiments of the present disclosure.

The band gap, which is designated as the difference between the highest occupied molecular orbital (HOMO) and the lowest unoccupied molecular orbital (LUMO), was calculated from the onset wavelength of the lowest energy absorption peak. The onset wavelength is designated as the negative tangent line of the lowest energy absorption peak that intersects with a linear tangent line of the absorption tail. FIG. 6 shows an example of the absorption spectrum of a concentrated solution of [CI][BETI] in DCM (curve 603) to illustrate the onset wavelength 606. An absorption onset at a higher wavelength corresponds to the minimum amount of energy which is needed for excitation of the electron from HOMO to LUMO. In other words, this is the energy for electronic transition from ground to excited state. A 3.4 eV value of the band gap in DCM was determined from:

$$E_g(\text{eV}) = \frac{1240}{\lambda(\text{nm})}. \tag{1}$$

Fluorescence Spectroscopy.

Figure 7A:
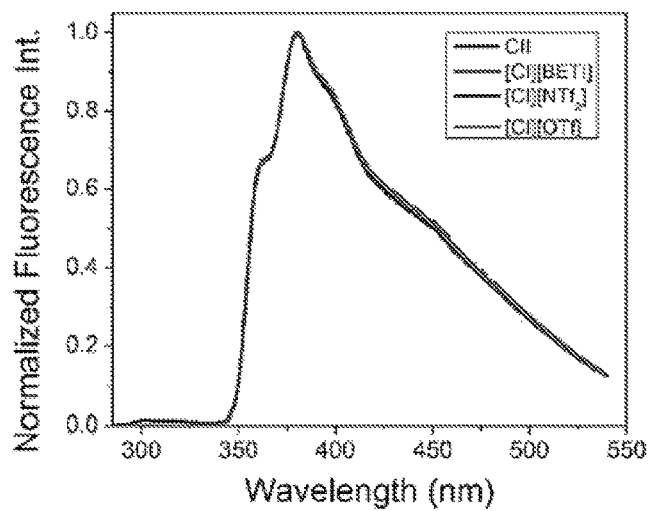
Figure 7B:
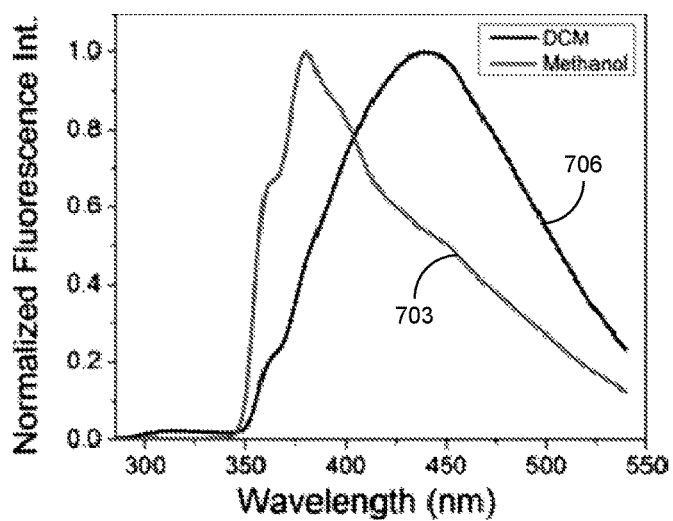

Fluorescence emission spectra of CII, [CI][OTf], [CI][NTf$_2$] and [CI][BETI] in methanol were recorded at an excitation wavelength of 275 nm as depicted in FIG. 7A. As can be seen, the emission spectrum was consistent for all of the carbazole-based GUMBOS. As illustrated by the fluorescence emission of [CI][NTf$_2$] in methanol (curve 703) and DCM (curve 706) in FIG. 7B, a broad emission spectrum was observed for all carbazole-based GUMBOS with a $\lambda_{max}$ at 440 nm in DCM and at 375 nm in methanol. This broadness may be attributed to the presence of the imidazole ring within the carbazole unit. An excitation wavelength-dependent fluorescence for imidazolium-based ILs has been reported. Similar behavior was observed in the current study as well, although the precise origin of the emission is still a matter of debate. FIG. 7C provides a representation of the fluorescence emission spectrum of [CI][BETI] (curve 709), which overlaps with the fluorescence spectrum of carbazole (curve 712) and imidazole (curve 715) upon excitation at the same wavelength ($\lambda_{ex}$ at 275 nm). The peak between the two suggests that the broadness in the emission spectrum of [CI][BETI] arises from a combination of two units.

The excitation spectra were measured using respective emission wavelengths of 385 and 440 nm in methanol and DCM. These spectral data are presented in the table of FIG. 8 and the absorption spectra 903 and fluorescence emission spectra 906 of [CI][BETI] in DCM with excitation $\lambda_{ex}$ at 275 nm illustrated in FIGS. 9A and 9B. As can be seen, the emission spectra and excitation spectra were not mirror images. The larger bandwidth of the fluorescence emission spectrum 906 may be attributed to incorporation of the imidazolium emission into the emission spectrum, while such changes were not observed in the excitation spectra.

A large Stokes shift of 105 nm was observed in DCM as illustrated in FIG. 10, which produces reduced fluorescence emission 1006. A significant increase in the Stokes shift was observed after addition of the imidazole ring onto the carbazole and may be the result of intramolecular charge transfer (ICT). The Stokes shift was calculated for each intermediate compound during synthesis. After addition of the alkyl group at the N position, the Stokes shift was the same as observed in carbazole alone. However, it drastically increased after the addition of the imidazole group at the third position of the carbazole. Hence, the Stokes shift may be attributed to the C—N bond of the carbon at the third position of carbazole, which is attached to the nitrogen of imidazole. Such a large Stokes shift has been previously identified in cyanine-based dyes as a result of ICT due to the formation of C—N bonds. The broadness of the emission spectra 1006 may also be attributed to the formation of an ICT state which emits in the blue region of the spectrum. Red and green emission may be observed, due to broadness by attaching different groups at carbazole.

Quantum Yield Measurements.

Absolute quantum yields were measured for all carbazole-based GUMBOS using an integrating sphere. The reported value of quantum yield for carbazole is 0.4, which is consistent with the value obtained using the integrating sphere. Quantum yields were also obtained using a relative method employing carbazole as the standard. Both approaches showed very high quantum yields for GUMBOS with [OTf], [NTf$_2$], and [BETI] counteranions. In this study, the reasons for enhanced measured quantum yields may be attributed to the large Stokes shift. High quantum yields with polymeric derivatives or with bulky organic compounds of carbazole have been previously reported in the literature. The primary advantage of GUMBOS-based materials is that it is possible to achieve these enhanced quantum yields using small molecules with simple changes in counteranions. Note that these quantum yields can also tuned, as reflected in the data presented in the table of FIG. 8.

Fluorescence Lifetimes.

Fluorescence lifetime measurements were performed in two solvents (MeOH and DCM). Fluorescence lifetime decays of the three carbazoleimidazole-based GUMBOS were best fit to a bi- or triple exponential decay, and the contributions to fluorescence in each case were determined to be primarily from two states. FIGS. 11A and 11B show tables of lifetime measurements of GUMBOS in DCM and methanol, respectively. The shorter lifetime component in each GUMBOS may be attributed to emission from the excited singlet state (1.9-3.4 ns in DCM and 94-133 ps in MeOH), while the slower component may be ascribed to emission from the charge transfer state (6.4 ns in DCM, 4.8 ns in MeOH). In methanol, the contribution from the third component is minor and could be the result of a back transition between the ICT and S$_1$ state. In previous studies, it has been observed that substitution of an electron-withdrawing substituent at the third position leads to a decrease in fluorescence lifetime from 7.33 ns (unsubstituted carbazole) to 350 ps. Thus, it is likely that the enhanced conjugation due to substitution of an imidazolium unit leads to a decrease in fluorescence lifetime from the S$_1$ state into the picosecond regime. The relatively shorter lifetime of the S$_1$ state in [CI][NTf$_2$] as compared to the other GUMBOS explains the lower quantum yield value of [CI][NTf$_2$].

Solid Film Studies.

Solid films were prepared from each GUMBOS, and their spectral properties were studied. Various solution techniques (such as, e.g., drop casting, spin coating, inkjet, and electrospray) were employed to obtain continuous, homogeneous, stable, and good solid films. For organic compounds, the vacuum deposition method is a well-established technique for acquiring thin films for OLEDs. However, since GUMBOS have low vapor pressures, this approach was not suitable for the materials. For these materials, it was determined that electrospray methods produced good quality films and also offered the best size control of droplets. These solid films were then characterized by use of SEM imaging and also by use of fluorescence microscopy. Results are shown in FIGS. 12A and 12B, which show an SEM image and an epifluorescence image of a [CI][BETI] film deposited on quartz, respectively.

The fluorescence emission was studied for these thin films. In the experiments, red-shifted fluorescence emission maxima were observed which attributed to dye aggregation as tabulated in the table of FIG. 13A. FIG. 13B illustrates the fluorescence emission of [CI][NTf$_2$] in bulk (curve 1303) and in solid film (curve 1306) with excitation $\lambda_{ex}$ at 275 nm. Intermolecular forces arising from electrostatic, π-π stacking, and van der Waals interactions in GUMBOS produced a relatively homogeneous film as suggested in FIGS. 12A and 12B.

Photo and Thermal Stability Tests.

Photostability and thermal stability are important factors for any dyes developed for use in OLEDs. An emitting material with significantly high photo- and thermal stability would enhance the life and broaden the applications of such materials under a variety of conditions. All GUMBOS investigated in the present study exhibited extremely interesting properties in response to light exposure. FIG. 14 illustrates the photostability of carbazole-based GUMBOS. An increase in photostability was actually observed for [CI][BETI] (curve 1403), whereas [CI][NTf$_2$] (curve 1406) and [CI][OTf] (curve 1409) underwent fairly stable fluorescence upon irradiation for more than 3000 s. Such an increase in photostability may be attributed to irradiation-induced changes in aggregation.

FIG. 15A illustrates the thermal stability of [CI][BETI] in methanol. Examination of data from temperature-dependent fluorescence measurements suggested that the fluorescence emission intensity continuously decreased by 25% with an increase in temperature from about 20° C. to about 60° C., as shown in FIG. 15B. However, this sample showed recovery of its original fluorescence intensity after cooling back to 20° C. from 60° C. FIG. 15C shows the fluorescence emission spectra of [CI][BETI] before and after temperature scan. No change in the photoluminescence spectra were observed before and after heating. This demonstrates that the GUMBOS compounds are quite stable toward heat and light.

Electrochemistry.

Electrochemical properties of these GUMBOS were evaluated by use of cyclic voltammetry. All solutions were prepared in DCM, and 0.1 M TBAPF6 was used as the supporting electrolyte. Cyclic voltammograms were recorded at a scan rate of 0.1 V/s. The potential of the working electrode was scanned to a positive value within the solvent window limit in order to acquire the oxidation peak of the carbazole unit in these compounds. The measured cyclic voltammograms generally displayed oxidation peaks, reflecting the formation of a di-cation. CII exhibited multiple electron transfer processes, which may be attributed to oxidation and reduction of iodide. This redox reaction was not seen in other GUMBOS having hydrophobic anions, e.g., [OTf], [NTf$_2$], and [BETI]. FIG. 16A illustrates the cyclic voltammograms for CII, [CI][NTf$_2$] and [CI][BETI] in DCM at 0.1 Vs$^{-1}$. This also verifies that the products are pure and little or no iodide remains after the ion exchange reaction. Note that these potentials can be measured at the peak positions or at the peak onset. The values of oxidation potentials obtained were recalculated versus a ferrocene/ferrocenium internal reference electrode. The redox potential for Fc/Fc+ was measured using the cyclic voltammograms. The cyclic voltammograms were analyzed in order to determine anodic peak potentials, which were later used to calculate the highest occupied molecular orbital (HOMO) energy level using:

$$E_{HOMO}(eV) = -1e^-[E_{pa}(V \text{ vs } Fc^{3+}/Fc) + 4.8(V \text{ } Fc^+/Fc \text{ vs zero})]. \quad (2)$$

These values were determined using a ferrocene reference, where $E_{pa}$ is the anodic potential. The energy of the HOMO is ultimately based on the absolute value of the normal hydrogen electrode (NHE). The values of HOMO energy levels for the GUMBOS were obtained using Equation (2) and tabulated in the table of FIG. 16B. The band gap ($E_g$ EC) can be measured as the difference in energy level between LUMO and HOMO as:

$$E_g(eV) = -(E_{HOMO}(eV) - E_{LUMO}(eV)). \quad (3)$$

The absorption spectral band gap and electrochemical HOMO energy levels were used to evaluate the LUMO energy level (Equation (3)). The lowest unoccupied molecular orbital (LUMO) energy levels were computed, and data are presented in the table of FIG. 16B. These values are quite similar for different GUMBOS, as the oxidation potential is primarily attributed to oxidation of the cationic carbazole unit since the anion does not have any redox characteristic. The HOMO energy levels of the GUMBOS are lower than the ITO HOMO energy level (4.70 eV), and the LUMO energy levels lie above the electron transport material (TBPI (1,3,5-tris(N-phenylbenzimidazol-2-yl)benzene, LUMO 2.70 eV). From an electronic perspective, carbazole-based GUMBOS can perform as emitters for use in OLEDs.

Computational Study.

DFT/TDDFT calculations provide additional understanding of the structural, electrochemical, and optical properties of the GUMBOS studied here. Optimized geometries revealed planar carbazole substituents, while the imidazole moiety had a twist. In all systems investigated, the HOMO was located primarily at the carbazole substituent, and the LUMO distributed over the imidazolium moiety. FIGS. 17A and 17B graphically illustrate the calculated HOMO and LUMO structures for [CI][BETI], respectively. The band gap computed using DFT/TDDFT is tabulated in the table of FIG. 16B. In all cases, the DFT calculations overestimated the HOMO-LUMO band gap, while the TDDFT results were in excellent agreement with the experimental results.

Conclusion

Carbazole-based GUMBOS have been synthesized using a very simple procedure. These GUMBOS exhibited high absorbance and excellent luminescence properties in combination with high quantum yields and excellent photo- and thermal stability. These compounds possess broad emission characteristics in the visible region and demonstrate good quantum yields. A blue emissive material with appropriate combination of properties has been achieved in a very small molecule without the need for synthesis of large molecules involving multiple steps and low yields. A very simple approach has been used to tune the physicochemical properties of these compounds. The tunability in quantum yields and thermal stability of GUMBOS was controlled by use of counteranions. Evaluation of the spectral and electrochemical properties, as well as computed band gaps, suggest the potential use of these compounds for optoelectronic applications and as emitting materials for use in OLEDs. The high chemical stability and photostability reported for these compounds ensure the long life needed for OLEDs.

Supporting Information

3-Bromocarbazole (1)

To DMF (67 ml) was added carbazole (10 g, 59.80 mmol) and mixture was stirred at room temperature for 15 minutes. N-bromosuccinimide (10.6 g, 59.56 mmol) in DMF (100 ml) was added dropwise at 0° C. The mixture was allowed to warm to room temperature and stirred for two hours. White precipitates were formed after the mixture was poured into water. The precipitates were filtered and dissolved in dichloromethane. The organic layer was washed with water to remove water soluble impurities. The organic fraction was dried over anhydrous sodium sulfate and the solvent was removed under reduced pressure. The resulting white solid was purified by recrystallization from ethanol to give colorless crystals (10.65 g, 72% yield). $^1$H-NMR (CDCl$_3$, 400 MHz): δ 8.34 (bs, 1H), 8.15 (d, J=7.8 Hz, 1H), 7.48 (d, J=8.2, 1H), 7.45 (m, 1H), 11.42 (s, 1H).

(MS, ESI) m/z 246 (M$^+$).

N-Ethylhexyl-3-bromocarbazole (2)

Sodium hydride (1.3 g, 60% w/w dispersion in mineral oil, 33.9 mmol) was added slowly to a mixture of 3-carbazole (6 g, 24.2 mmol) and anhydrous DMF (50 ml). After 30 minutes 2-ethylhexyl bromide (6.04 g, 31.3 mmol) was added. The reaction was quenched with water, after stirring at room temperature for 24 hours and extracted with CH$_2$Cl$_2$. The organic layer was dried over anhydrous sodium sulfate. Evaporation of the solvent under vacuum resulted in a yellow residue. The residue was purified by column chromatography using 10% ethyl acetate/hexane mixture as an eluent to give pure compound as colorless viscous (8.22 g, 95% yield). $^1$H-NMR (CDCl$_3$, 400 MHz): δ 8.20 (d, J=1.6 Hz, 1H), 8.05 (d, J=7.8 Hz, 1H), 7.52 (dd, J=8.6, 1.8, 1H), 7.46 (d, J=8 Hz, 1H), 7.40 (t, 1H), 7.38 (s, 1H), 4.14 (m, 1H), 2.0 (m, 2H), 1.78 (m, 2H) 1.50-1.27 (m, 8H), 0.91 (t, 3H), 0.87 (t, 3H).

(MS, ESI) m/z 358 (M$^+$).

N-Ethylhexyl-3-imidazolium carbazole (3)

A mixture of N-ethylhexyl-3-bromocarbazole (6 g, 16.7 mmol), imidazole (1.24, 18.3 mmol), 1,10-phenanthroline (0.65 g, 3.6 mmol), CuI (0.31 g, 1.66 mmol) and K$_2$CO$_3$ (5.75 g, 0.042 mmol) in anhydrous DMF (50 ml) was stirred for 30 minutes at room temperature and then refluxed at 150° C. under N$_2$ for 30 hours and cooled to room temperature. DMF was removed under high vacuum and temperature. The resulting brown solid was dissolved in water and extracted with dichloromethane. The organic extract was then dried over anhydrous Na$_2$SO$_4$. Dichloromethane was removed under high vacuum. The impure product was purified by silica gel column chromatography using ethyl acetate: hexane (1:1) to obtain the pure compound as light brown solid (5.24 g, 91% yield).

$^1$H-NMR (CDCl$_3$, 400 MHz): δ 8.11 (d, J=7.76 Hz, 1H), 8.06 (s, 1H), 7.89 (s, 1H), 7.52-7.42 (m, 4H), 7.27 (s, 1H), 7.26 (t, 1H), 7.24 (s, 1H), 4.21 (m, 1H), 2.04 (m, 4H), 1.27-1.26 (m, 6H), 0.93 (t, 3H), 0.86 (t, 3H).

(MS, ESI) m/z 346 (M$^+$).

N-Ethylhexyl-3-(3-methylimidazolium iodide) carbazole (4)

N-Ethylhexyl-3-imidazolium carbazole (1.98 g, 5.49 mmol) was dissolved in DMF in a 500 ml round bottom flask. After stirring for few minutes, iodomethane (0.68 g, 10.98 mmol) was added and refluxed at 60° C. for 24 h. After 24 hours, DMF was removed under high vacuum. The crude reaction mixture was purified by silica-gel column chromatography. The column was eluted with methanol: dichloromethane (1:9). The solvent was evaporated at reduced pressure to give the needed compound as white solid (2.11 g, 79% yield).

$^1$H-NMR (CDCl$_3$, 400 MHz): δ 10.29 (s, 1H), 8.44 (d, J=1.92 Hz, 1H), 8.21 (d, J=7.8 Hz, 1H), 7.73-7.69 (m, 2H), 7.59-7.43 (m, 3H), 7.41 (d, J=8 Hz, 1H), 7.37 (t, 1H), 4.22 (s, 3H), 2.06 (m, 2H), 1.98 (m, 4H), 1.28-1.22 (m, 6H), 0.89-0.82 (m, 6H).

(MS, ESI) m/z 360 (M$^+$).

Carbazoleimidazolium trifluoromethanesulfonate [CI][OTf] (5)

Compound 4 (0.5 g, 1 mmol) was anion exchanged with sodium trifluoromethanesulfonate (0.19 g, 1.3 mmol) in a biphasic solution where CII was dissolve in DCM while a saturated solution of NaOTf was prepared in water. The biphasic solution of DCM and water was stirred for 3-4 days, the lower layer of DCM was separated from water and washed with water several times to remove the by-product (sodium salt of iodide) which was highly soluble in water. The DCM was evaporated under high vacuum and freeze-dried to remove small amounts of water. The product was obtained as yellow solid (0.48 g, 93% yield).

$^1$H-NMR (CDCl$_3$, 400 MHz): Carbazoleimidazolium cation: δ 9.72 (s, 1H), 8.57 (d, J=2.16 Hz, 1H), 8.19 (d, J=7.6 Hz, 1H), 7.95-7.77 (m, 2H), 7.65 (m, 1H), 7.29 (t, 1H), 4.35 (s, 3H), 3.96 (m, 2H), 1.99 (m, 4H), 1.31-1.16 (m, 6H), 0.84-0.76 (m, 6H);

$^{19}$F-NMR: (CDCl$_3$, 250 MHz) Trifluoromethanesulfonate: δ −79.22.

(MS, ESI$^+$) m/z 360, (MS, ESI$^-$) m/z 149.

Carbazoleimidazolium bis(trifluoromethylsulfonyl)imide [CI][NTf$_2$] (6)

Compound 4 (0.1 g, 0.21 mmol) was anion exchanged with LiNTf$_2$ (0.07 g, 0.24 mmol) followed the same procedure as described in 5 above. The product was obtained as yellow viscous solid (0.1 g, 76% yield).

$^1$H-NMR (CDCl$_3$, 400 MHz): Carbazoleimidazolium cation δ 9.90 (s, 1H), 8.34 (d, J=1.96 Hz, 1H), 8.19 (d, J=7.8 Hz, 1H), 7.62-7.56 (m, 2H), 7.54-7.52 (m, 3H), 7.47 (d, J=8.28 Hz, 1H), 7.32 (t, 1H), 4.22 (s, 3H), 2.34 (m, 2H), 1.40 (m, 4H), 1.28-1.26 (m, 6H), 0.95-0.85 (m, 6H).

(MS, ESI$^+$) m/z 360, (MS, ESI$^-$) m/z 280;

$^{19}$F-NMR: (CDCl$_3$, 250 MHz): bis(trifluoromethylsulfonyl)imide: δ −78.78.

Carbazoleimidazolium bis(pentafluoroethylsulfonyl)imide-[CI] [BETI] (7)

Compound 4 (0.1 g, 0.21 mmol) was anion exchanged with LiBETI (0.096 g, 0.24 mmol) followed the same procedure as described in 5 above. The product was obtained as yellow solid (0.15 g, 98% yield). MP: if solid (check).

$^1$H-NMR (CDCl$_3$, 400 MHz): Carbazoleimidazolium cation: δ 10.39 (s, 1H), 8.37 (d, J=2 Hz, 1H), 8.18 (d, J=7.48 Hz, 1H), 7.58-7.42 (m, 2H), 7.40 (d, J=8 Hz, 1H), 7.38 (t, 1H), 4.16 (s, 3H), 4.05 (m, 2H), 1.97 (m, 4H), 1.36-1.25 (m, 6H), 0.90-0.85 (m, 6H);

$^{19}$F-NMR: (CDCl$_3$, 250 MHz): δ −117.64, −79.33.

(MS, ESI) m/z 360 (M$^+$), (MS, ESI$^-$) m/z 380.

Example 2

GUMBOS composed of a carbazoleimidizolium-based cation and various hydrophobic anions have been synthesized and characterized. Analysis of the absorption spectra of these compounds indicate significant increases in energy gaps between the first two excited singlet states, which results in inhibition of internal conversion from the S$_2$ to S$_1$ states. Detailed studies of the spectral properties of these compounds support emission from multiple excited states including possible emission from the second excited singlet state ($S_2$ emission) in combination with an intramolecular charge transfer state. This conclusion is also consistent with fluorescence lifetime data, which suggest fluorescence emission from multiple electronic excited states. In addition, theoretical calculations of the excited states support these conclusions.

Emission from the second excited singlet state ($S_2$ emission) is an unusual phenomenon as it violates Kasha's rule, which dictates that emission should occur from the lowest excited state of a molecule of a given multiplicity. This suggests that emission from a higher excited state is rare due to a relatively fast non-radiative internal conversion process, which occurs among electronic excited states of the same multiplicity. However, if the first two excited states of the same multiplicity do not maintain a large energy gap, the result is a more rapid non-radiative decay as compared to radiative emission from the second excited singlet state. Nevertheless, anomalous emission from second excited singlet states were observed and reported in azulene ("Anomalous light emission of azulene" by Beer et al., *J. Chem. Phys.*, vol. 23, no. 8, pp. 1390-1391, 1955). In addition, $S_2$ fluorescence emission has also been observed in a few other classes of compounds such as porphyrin, thione, and carbazole. Two primary reasons have been attributed to $S_2$ emission from such compounds: (1) a wide energy gap between the first two excited singlet states that inhibits internal conversion; and (2) the symmetry of the geometries in the excited states.

A wide energy gap between the first two excited singlet states reduces vibronic coupling between these excited states, which diminishes the non-radiative process (internal conversion). Inhibition of non-radiative internal conversion leads to radiative emission from the second excited singlet state as observed in the aforementioned compounds. Such molecules have received considerable attention due to their utility for probing the molecular environment (e.g., polarity, viscosity, temperature). This results from dependence of these processes on the environment, and thus remarkable changes in the ratio of first excited singlet state ($S_1$) and second excited singlet state ($S_2$) emission intensities are observed in the presence of different media. However, a distinct challenge is examination of the photophysical properties of these molecules in higher excited states. This problem arises from rapid deactivation of the excited state, as well as other energy and electron transfer processes which may occur in the excited state. Thus, spectroscopic tools such as ultrafast transient absorption spectroscopy can provide valuable information about these molecules in the excited states. Studies in the literature for anomalous $S_2$ emission have been in regard to solid phase organic molecules, not for solid phase organic salts (GUMBOS).

GUMBOS and ionic liquids have tunable properties and can be used in a multitude of applications. While ionic liquids have been demonstrated to have applications in a variety of areas such as solvents, synthesis, pH sensors, colorimetric sensors, electrochemistry, and others, GUMBOS are more applicable to materials chemistry. Herein, observation of an $S_2$ fluorescence emission phenomenon in GUMBOS is disclosed. In this study, a carbazoleimidazolium-based iodide salt was synthesized, and subsequently followed with ion exchange reactions to yield two GUMBOS containing different counter anions, specifically trifluoromethanesulfonate (OTf) and bis(trifluoromethylsulfonyl)imide ($NTf_2$).

Carbazole is used for this study, which is a p-type semiconductor with two excited states in the absorption spectra and may have applications as semiconductor lasers. However, the parent compound does not exhibit any emission from higher excited state ($S_2$ emission) due to the small energy gap between the second excited singlet state ($S_2$) and the first excited singlet state $S_1$. To increase the energy gap, an imidazolium ring was attached at the third carbon of carbazole which produced enhanced conjugation. Two different counteranions were substituted at the carbazoleimidazolium cation, which produced tunable thermal stability with improved photostability. These GUMBOS were synthesized in order to increase the energy gap between the second and first excited singlet states by improving conjugation and through formation of an intramolecular charge transfer complex between the carbazole and imidazolium units. The spectral properties of these compounds were studied in order to provide estimates of excited state energies. The absorption spectra, fluorescence emission spectra, and excitation-emission matrix were recorded for each GUMBOS in order to provide better insight into spectral properties. Lifetime measurements at various excitation and emission wavelengths were also obtained in order to understand the contributions of emission processes from various excited states to the ground state, as well as between the two excited states in these GUMBOS. Quantum mechanical calculations were performed to ascertain symmetry of the orbitals and to estimate the energy gap between the excited states. Data obtained from these studies were consistent with the experimental observations.

Experimental Method

Materials.

Sodium trifluoromethanesulfonate (NaOTf), and lithium bis(trifluoromethylsulfonyl)imide ($LiNTf_2$), were purchased from Sigma Aldrich and used as received. Tetrahydrofuran (THF) was purchased from Macron chemicals and dicholoromethane (DCM) was purchased from J. T Baker. Triply deionized water (18.2 MΩ cm) was obtained by use of an Elga model PURELAB ultra water-filtration system and was used for all ion exchange reactions.

Instrumentation.

MPA 160 and MPA 161 DigiMelt SRS (Stanford Research System) were used to determine melting points. The phase transition thermal characteristics of these compounds were studied by use of a Q100 differential scanning calorimeter (DSC, TA instruments, New Castle, Del.). A few milligrams of the GUMBOS were weighed into an aluminum crucible and sealed with an aluminum lid. The resultant sample was scanned from −40 to 150° C. using a rate of 5° C. $min^{-1}$ under nitrogen flow of 50 ml $min^{-1}$. Thermal stability of the GUMBOS were determined by heating a few milligrams at a scan rate of 10° C. $min^{-1}$ from 25 to 600° C. using a Hi Res Modulated TGA 2950 Thermogravimetric Analyzer.

A Shimadzu UV-3101PC and a UV-Vis-near-IR scanning spectrometer (Shimadzu, Columbia, Md.) were used for absorbance measurements. All fluorescence measurements were performed on a Spex Fluorolog-3 spectrofluorimeter (model FL3-22TAU3); JobinYvon, Edison, N.J.). A 0.4-cm path length quartz cuvet (Starna Cells) was used for fluorescence measurements. All fluorescence studies were performed using right angle geometry. A 0.4 cm path length quartz cuvet was used for absorbance measurements against an identical cell filled with THF as the blank solvent.

Fluorescence lifetimes were measured using a Fluoro-Cube spectrofluorimeter (model FluoroCube, HORIBA Scientific, Edison, N.J.) employing the time domain mode. A picosecond pulsed LED excitation source of 273 and 344 nm was used at 1 MHz, and emission collected at 309, 362, and 385 nm using a TBX detector. The time correlated single photon counting (TSCPC) mode was used for lifetime data acquisition with a resolution of 28 ps/Channel over a 100 ns TAC range.

Computational Details.

A Gaussian 09 program was used for all computations. The geometric structures of compounds were modelled using GaussView 5.0. Ground state geometries of each GUMBOS as a whole were optimized using density functional theory (DFT) and time dependent density functional theory (TDDFT) in the gas phase. A hybrid DFT Becke's three-parameter nonlocal exchange functional employing the correlation functional of Lee-Yang-Parr (B3LYP) was used for all calculations. A split valence basis set of 6-31+ G(d,p) was also employed. The choice of basis set with polarized and diffuse functions were used for a better description of electrons relatively far from the nuclei. Vibrational frequencies were analyzed in order to confirm the optimized structures as a local minima. Optimized structures were used for TDDFT by employing the same model chemistry (B3LYP/6-31+G (d,p)) to determine the lowest excitation energies corresponding to the HOMO-LUMO band gap.

Synthesis.

Synthesis of carbazoleimidazolium iodide was performed similar to the previously disclosed procedure. All synthesis details and characterization schemes have been presented previously. Two different GUMBOS were synthesized from carbazoleimidazolium iodide (CII) using a metathesis approach. Anion exchange was performed to replace the iodide ion with trifluoromethanesulfonate (OTf) and bis (trifluoromethylsulfonyl)imide (NTf$_2$) ions using a standard ion exchange protocol. A biphasic mixture of CII in dicholormethane (DCM) and sodium/lithium salts of OTf or NTf$_2$ in water was stirred for three to four days. After separation of the DCM layer from the water layer, the DCM was rinsed several times with water to remove entrained sodium/lithium iodide impurities. The DCM solvent was removed from the dissolved GUMBOS by use of a rotary evaporator, followed by removal of final traces of water using freeze drying. The final products were characterized using ESI-MS, 1H-NMR, and 19F-NMR. The structures of these two GUMBOS are shown in FIG. 18.

Physical Properties of GUMBOS.

Both GUMBOS were light yellow viscous materials. The melting points of these compounds were determined by use of two different approaches. Differential scanning calorimetry results for measurement of melting points were consistent with results obtained from physically observed meting points measured in capillaries filled with the compounds. These latter melting points were obtained by use of an MPA 160 and MPA 161 DigiMelt SRS (Stanford Research System). The carbazoleimidazolium iodide (CII) is a white solid with a very high melting point. After exchange of the iodide ion with bulky hydrophobic anions, the melting points ($T_m$) of the resulting compounds were lowered substantially and these materials were then consistent with the standard definition of GUMBOS (M.P. 25-250° C.). The drops in melting points after anion exchange with relatively large anions may be attributed to frustrated packing between the oppositely charged counterions. In addition, a long alkyl chain may also be responsible for acquiring amorphous materials with a significant decrease in melting point. The [CI][NTf$_2$] compound is a viscous jelly like liquid; hence, was difficult to fill in a capillary to record the melting point. Thermal decomposition temperature (Td) was significantly improved in the resulting GUMBOS and X-ray diffraction (XRD) data revealed that these GUMBOS are amorphous FIG. 19 shows the XRD for [CI][NTf$_2$], and the table of FIG. 19B illustrates physical properties of CII and GUMBOS.

Results

UV-Vis Spectroscopic Studies.

Carbazole and its derivatives can display two major absorption bands, representing respective transitions from the ground state to the first excited singlet state ($S_1$) and the second excited singlet state ($S_2$). Thus, at least two peaks are expected in the absorption spectra of carbazoleimidazolium-based GUMBOSsince the counter anions employed in this study do not contribute to absorbance in the wavelength range of the UV-Vis spectra of these compounds. The normalized absorption UV-Vis spectra of carbazole (curve 2003) and the derived carbazole-based GUMBOSCII (curve 2006), [CI][OTf] (curve 2009) and [CI][NTf$_2$] (curve 2012), in THF, are illustrated in FIG. 20.

Interestingly, notable shifts in wavelength corresponding to transitions to the first excited singlet state ($S_1$=335 nm) and the second excited singlet state ($S_2$=275 nm) were observed in the absorption spectra of these GUMBOS relative to the parent carbazole compound ($S_1$ at 320 nm and $S_2$ at 293 nm). A bathochromic shift of $S_1$ and a hypsochromic shift of $S_2$ as compared to the parent compound may be attributed to extended conjugation in these GUMBOS as a result of attaching the imidazolium ring at the third carbon of carbazole. Thus, this structural change leads to a significant increase in energy gap between the first two excited singlet states of these GUMBOS. In other words, these finding can be expressed as:

$$(\Delta E_{S2-S1})_{carbazoleimidazole\ GUMBOS} > (\Delta E_{S2-S1})_{carbazole}. \quad (4)$$

Fluorescence Spectroscopic Studies.

Fluorescence emission spectra of the GUMBOS in THF were recorded at two different excitation wavelengths. In the previous studies, the effect of incorporating an imidazolium ring at the third carbon of carbazole was investigated. It was found that this change in structure leads to the formation of an intramolecular charge transfer state, which then results in a large stokes shift. When excited at the $S_1$ maxima (335 nm), it was observed that the fluorescence emission spectra, with emission maxima at 385 nm, were very intense and broad as compared to the absorption spectra. Broadening of the emission spectra may be ascribed to emission from two different excited states, i.e. the first singlet excited state ($S_1$ emission) and the intramolecular charge transfer state (emission from ICT). A broad peak with a clearly defined maxima at 385 nm was assigned to emission from ICT, while the shoulder observed at 362 nm, was assigned to a radiative transition from the $S_1$ state.

When the excitation wavelength was set at the $S_2$ absorption band (275 nm), a similar broad highly intense spectrum was attained with an additional small peak at shorter wavelength (305 nm) as shown in FIGS. 21A and 21B. FIG. 21A illustrates the fluorescence emission spectra of a 5 µM solution of [CI][NTf$_2$] in THF at two different excitation wavelengths $\lambda_{ex}$, $S_1$ (curve 2103 at 335 nm) and $S_2$ (curve 2106 at 275 nm). FIG. 21B illustrates the normalized fluorescence emission spectra of CII (curve 2109) and [CI][OTf] (curve 2112) in THF, $\lambda_{ex}$ at 275 nm. This high energy fluorescence peak was not observed when GUMBOS were excited at the $S_1$ state.

This additional peak at lower wavelength, with low intensity, may arise from emission of the second excited singlet state ($S_2$ emission), which is termed an anomalous emission process since it contradicts Kasha's rule of emission from the first excited state. The $S_2$ emission may be attributed to an absence or slow rate of internal conversion between the first two excited singlet states ($S_2$ and $S_1$) owing to an increase in energy gap and the small vibrational overlap between these two excited states. One criterion for $S_2$ emission is an energy gap greater than 3000 cm$^{-1}$. However, $S_2$ emission does not solely depend on the energy gap between these two states. The value of the energy gap calculated between the two excited singlet states for these GUMBOS was 6513 cm$^{-1}$. This value for the present GUMBOS is extremely high relative to the stated criterion for $S_2$ emission ($\Delta E > 3000$ cm$^{-1}$).

Examination of the absorption spectra showed a significant wavelength shift in opposite directions for the two excited states, $S_2$ and $S_1$ (about 60 nm separation). In comparison, the parent carbazole compound had a gap of only about 30 nm. Thus, the primary reason for the observed dual emission in these GUMBOS may be attributed to the wide energy gap between the first two excited singlet states. Using the energy gap law, the rate of internal conversion can be estimated as shown by:

$$k_{IC} \propto \exp(-\beta \Delta E), \quad (5)$$

where $\beta$ is a constant and $\Delta E$ is the energy difference between the two excited states (energy gap). The inverse relationship between the rate of internal conversion and the energy gap between the first two excited states can be used to support the inferred inhibition of the radiationless deexcitation process (IC) with an increase in the energy gap. It therefore can be reasoned that the large energy gap is not the only reason for the observed $S_2$ emission. For example, the $S_2$ emission can also depend on symmetry restrictions and spin multiplicity. This is supported by reports in the literature where $S_2$ emission was observed despite a small energy gap. For example, the energy gap for diphenyloctatetrene is about 3000 cm$^{-1}$ and $S_2$ emission can still be observed. This reported observation was explained by invoking symmetry allowed transitions. The energy gap between the first two excited singlet states of the GUMBOS developed in this disclosure is quite large when compared to the reported criteria. However, it is useful to examine the structural symmetry of these molecules. Thus, quantum mechanical calculations were conducted for a better understanding of our observations.

Studies of excitation-emission matrices (EEM) were designed to gain additional information regarding the observed dual emission, shape, and broadness of the peaks. The compounds were excited at different wavelengths (e.g., 250-335 nm using intervals of 5 nm), and the measured fluorescence emissions were recorded. Within the EEM, a broad fluorescence emission peak at 385 nm with a shoulder at 362 nm was observed, while no emission was observed within the lower wavelength region from the $S_2$ state when the excitation wavelengths were in the range of the $S_1$ absorption band (335 nm). FIG. 22 illustrates an example of the excitation-emission spectra (EEM) of the 5 μM solution of [CI][NTf$_2$] in THF. If this additional peak arises from $S_2$ emission, then $S_2$ emission should not occur in these GUMBOS when excited to the $S_1$ state (by longer wavelengths). This is because molecules excited at these longer wavelengths can only reach the $S_1$ state, but are unable to reach the $S_2$ state due to insufficient excitation energy.

Examination of the EEM also did not produce any observed excitation dependent emission from the $S_1$ and ICT states. The fluorescence spectra were observed to be broad when excited at different wavelengths in the region of $S_1$. However, intensity changes were perceived to be the result of fewer molecules reaching the first excited singlet state when excitation wavelengths were shifted from the excitation maxima. Furthermore, another peak in the shorter wavelength region was observed when excited in the region of the $S_2$ maxima (see FIG. 16). This peak is assigned to $S_2$ emission. Thus, exciting these GUMBOS in the region of the $S_2$ maxima produces emission from the $S_1$, ICT as well as from one higher energy level which is likely the $S_2$ excited state. While various derivatives of carbazole have been examined, only certain derivatives of the carbazole molecule can produce dual emission ($S_2$ and $S_1$ emission). The current data explains the possibility of emission from more than one excited state in the GUMBOS systems based on carbazole.

Referring back to FIG. 20, the acquired absorption spectra clearly reflected a higher molar extinction coefficient for the $S_2$ state as compared to the $S_1$ state. In contrast, the fluorescence emission spectra revealed strong fluorescence emission intensity from the $S_1$ or ICT states relative to the emission intensity of $S_2$. This decrease in fluorescence emission intensity of $S_2$ may be ascribed to intramolecular energy transfer from $S_2$ to $S_1$ as a result of the moderate overlap between the $S_2$ fluorescence emission and the $S_1$ absorption in these GUMBOS as depicted in FIG. 23, which illustrates the fluorescence emission (curve 2303) and absorption (curve 2306) spectra of 3 μM solution of [CI][NTf$_2$] GUMBOS in THF. The spectral overlap integral ($J(\lambda)$) can be estimated using:

$$J(\lambda) = \frac{\int_0^\infty \varepsilon(\lambda) f(\lambda) \lambda^4 d\lambda}{\int_0^\infty f(\lambda) d\lambda}, \quad (6)$$

where $\varepsilon$ is the molar extinction coefficient of the acceptor, $f(\lambda)$ is the normalized emission spectrum of the donor, and $\lambda$ is the wavelength. The overlap integral value calculated for [CI][NTf$_2$] was about $2.47 \times 10^{-15}$, which suggests the possibility of limited intramolecular Förster resonance energy transfer (FRET) between these two excited states. Since carbazole is a hole semiconductor, there is a high probability of an S2→ICT transition. A hole can be generated at the carbazole unit after intramolecular charge transfer, followed by immediate electron jumps from the higher excited states to fill this hole, similar to what is observed for organic light emitting diodes (OLEDs). The less intense fluorescence emission peak of $S_2$-$S_o$ may also be a transition from the $S_2$ to ICT state. In order to understand these multiple emission processes from different excited states, transient absorption experiments can be performed.

Fluorescence Lifetime Measurements.

The fluorescence lifetime decays of these GUMBOS were measured at different excitation and emission wavelengths to gain a better understanding of the various electronic transitions. These GUMBOS were excited at two different wavelengths, e.g. the first excited singlet state (Ex $S_1$ 344 nm) and the second excited singlet state (Ex $S_2$ 277 nm). Fluorescence was collected at three different wavelengths in order to provide better insight into the photophysical characteristics of emission from the different excited states. The measured emission wavelengths were set at 309 nm (possible $S_2$ emission), 362 nm ($S_1$ emission) and 385 nm (ICT emission). The resultant data were fit to a triple exponential decay, and the contributions from fluorescence in each case were determined to be primarily from three states. The table of FIG. 24 lists fluorescence lifetime data for a 10 μM solution of GUMBOS in THF at different excitation and emission wavelengths. The lifetime of $S_2 \rightarrow S_o$ emission was ascribed to 0.85-1.1 ns. This was based upon the observation that the contribution of this component decreased as the collection of emission wavelength shifted from a possible $S_2$ emission while the excitation wavelength was held constant at $S_2$.

In addition, the highest contribution of this component was noted when GUMBOS were excited at $S_2$ wavelength and the emission were collected at $S_2$. The two other components in the lifetime data were ascribed to a radiative transition from ICT→$S_o$ and $S_1$→$S_o$. The lifetime for ICT→$S_o$ can be estimated at about 8 to 9.5 ns, whereas 3-4 ns can be ascribed to the fluorescence from $S_1$→$S_o$ after a back transition between the ICT and $S_1$ state. A new component of shorter life time appeared when the excitation wavelength was set at 344 nm ($S_1$). The short 72 ps component in [CI][NTf$_2$] and 691 ps component in [CI][OTf] may be attributed to emission from an $S_1$→$S_o$ transition. It has been observed that substitution of an electron withdrawing group at the third position of carbazole leads to a drop in fluorescence lifetime from 7.33 ns (unsubstituted carbazole) to 350 ps from $S_1$→$S_o$. Therefore, improved conjugation may be due to substitution of an imidazolium unit into carbazole, leading to a decrease in the fluorescence lifetime of the $S_1$→$S_o$ state, into the picosecond timescale. Average lifetimes of the two GUMBOS ([CI][OTf] and [CI][NTf$_2$]) for $\lambda_{ex}/\lambda_{em}$ of 277/309 nm and 277/362 nm exhibit very close values. These values represent the average lifetimes of primarily the $S_2$ and $S_1$ states, respectively. However, the average lifetime for $\lambda_{ex}/\lambda_{em}$ of 277/385 nm, representing primarily the charge transfer state, are significantly different with nearly a three times shorter lifetime for [CI][NTf$_2$] as compared to [CI][OTf]. This suggests that variation of the counteranion affects the charge transfer state emission behavior.

Optimized Geometries of GUMBOS.

TDDFT calculations provide additional understanding of the structural, electrochemical, and optical properties of these new GUMBOS. Optimized geometries revealed that carbazole substituents tend to be planar, while the imidazole moiety is twisted. In all of these systems, the computed HOMO is located primarily at the carbazole unit and the LUMO distributes over the imidazolium moiety. FIGS. 25A and 25B illustrate frontier molecular orbital diagrams for the two GUMBOS ([CI][OTf] and [CI][NTf$_2$], respectively) representing intramolecular charge transfer process affected by counteranions. These molecular orbital diagrams represent electron densities of the ground and excited states. It is noted that the electron density can be completely removed from the carbazole unit and distributed into the imidazolium ring in [CI][NTf$_2$]. In contrast, there is only a slight shift of electron density toward the imidazolium ring in [CI][OTf]. Thus, the anions may be primarily responsible for the charge transfer process. Furthermore, it can be assumed that the intramolecular charge transfer is enhanced in the presence of a more hydrophobic anion. Symmetry in the orbitals is also observed for the ground and excited states, and it can be concluded that $S_1$ and $S_2$ absorption peaks are due to π-π* transitions.

The computed band gaps using TDDFT are tabulated in the table of FIG. 26A. In all cases, the TDDFT results (transition energies, excitation wavelengths, and oscillator strengths) are in excellent agreement with the experimental results. Two approximate excitation energies were observed for all GUMBOS as depicted in the table of FIG. 26A. The high oscillator strength represents a HOMO-1→LUMO transition, which corresponds to $S_o$→$S_2$. The first dipole-allowed electronic transitions correspond to promotion of an electron from HOMO→LUMO. This represents the $S_o$→$S_1$ transition, which has lower oscillator strength as observed in the experimental results. A molecular orbital diagram of [CI][NTf$_2$] representing the transitions is illustrated in FIG. 26B.

Conclusion

Carbazoleimidazolium-based GUMBOS with two different hydrophobic anions were synthesized and characterized. The hydrophobicity of the anions increased with an increase in size of the trifluoro chain and charge transfer also depends upon the respective counteranions. Enhanced tunable thermal and photostability, which is directly associated with the structure of the counteranions, were acquired in the resultant amorphous GUMBOS. The absorption peaks for the $S_1$ and $S_2$ transitions were observed to have a large shift due to extensive conjugation after addition of imidazole at the third carbon of carbazole. This shift of energy levels in the opposite direction increased the energy gap between two singlet excited states. The observed emission at lower wavelength (possible $S_2$ emission) in these GUMBOS, only when excited at $S_2$ state, was attributed to this significant increase in energy gap between the two excited states, in combination with enhanced symmetry. This significant increase in energy gap between these two states is responsible for suppression of the internal conversion process. Lifetime data supports our contention that fluorescence emission occurs from multiple excited states. Excited states energy levels obtained using theoretical quantum calculations are also in good agreement with the experimental results.

Supporting Information

Carbazoleimidazolium trifluoromethanesulfonate [CI][OTf].

Carbazoleimidazaolium iodide (CII) (0.5 g, 1 mmol) was dissolved in dicholoromethane (DCM). A saturated solution of sodium trifluoromethanesulfonate (0.19 g, 1.3 mmol) was prepared in water. These two solution were mixed together to perform anion exchange reaction in a biphasic solution. The biphasic solution of DCM and water was stirred for 3-4 days. After 4 days, the lower layer of DCM was separated from water and washed with water several times to remove the by-product (sodium salt of iodide) which was highly soluble in water. DCM was evaporated under high vacuum. After removing DCM, sample was freeze-dried to remove small amounts of water. The product was obtained as yellow solid (0.48 g, 93% yield).

$^1$H-NMR (CDCl$_3$, 400 MHz): Carbazoleimidazolium cation: δ 9.72 (s, 1H), 8.57 (d, J=2.16 Hz, 1H), 8.19 (d, J=7.6 Hz, 1H), 7.95-7.77 (m, 2H), 7.65 (m, 1H), 7.29 (t, 1H), 4.35 (s, 3H), 3.96 (m, 2H), 1.99 (m, 4H), 1.31-1.16 (m, 6H), 0.84-0.76 (m, 6H);

$^{19}$F-NMR: (CDCl$_3$, 250 MHz) Trifluoromethanesulfonate: δ −79.22.

(MS, ESI$^+$) m/z 360, (MS, ESI$^-$) m/z 149.

Carbazoleimidazolium bis(trifluoromethylsulfonyl)imide [CI][NTf$_2$].

Carbazoleimidazaolium iodide (CII) (0.1 g, 0.21 mmol) was anion exchanged with LiNTf$_2$ (0.07 g, 0.24 mmol) following the same procedure as described above. The product was obtained as yellow viscous jelly like liquid (0.1 g, 76% yield).

$^1$H-NMR (CDCl$_3$, 400 MHz): Carbazoleimidazolium cation δ 9.90 (s, 1H), 8.34 (d, J=1.96 Hz, 1H), 8.19 (d, J=7.8 Hz, 1H), 7.62-7.56 (m, 2H), 7.54-7.52 (m, 3H), 7.47 (d, J=8.28 Hz, 1H), 7.32 (t, 1H), 4.22 (s, 3H), 2.34 (m, 2H), 1.40 (m, 4H), 1.28-1.26 (m, 6H), 0.95-0.85 (m, 6H);

$^{19}$F-NMR: (CDCl$_3$, 250 MHz): bis(trifluoromethylsulfonyl)imide: δ −78.78.

(MS, ESI$^+$) m/z 360, (MS, ESI$^-$) m/z 280.

Example 3

The design, synthesis and characterization of carbazole-coumarin conjugated organic semiconducting small ionic compounds as new candidates for optoelectronics has been examined, particularly in organic light emitting diodes (OLEDs). In this study, substitution of 3-(2-benzimidazolyl)-7-(diethylamino)coumarin (Coumarin 7, BDC) to carbazole can tune the fluorescence emission of the substituted carbazoles to produce blue light emission and at the same time, will enhance the quantum efficiency of the resultant molecules. Incorporation of organic counter-anions bis(pentafluoroethylsulfonyl)imide (BETI), bis(trifluoromethylsulfonyl)imide (NTf$_2$), and trifluoromethanesulfonate (OTF) converted these molecules to compounds from a class of compounds characterized as GUMBOS, which represent organic salts with melting points in the range of 25 to 250° C. Conversion of organic compounds to their respective GUMBOS generally enhances the compound's longevity due to their inertness, and increased hydrophobicity after the conversion. Experimental data confirmed the semiconducting and luminescent properties of these materials. The highest occupied molecular orbital energies ($E_{HOMO}$), lowest unoccupied molecular orbital energies ($E_{LUMO}$), and HOMO-LUMO band gap of these materials were found as 5.04 (±0.03) eV, and 2.00 (±0.02) eV, and 3.03 (±0.02), respectively. Photo-stability of these compounds was found to be very high and quantum yields of these materials were in the range of 87-96% with photon yields of emission primarily in the blue region of the electromagnetic spectrum.

Carbazole-based organic molecules, either in polymeric forms or as small molecules can be widely exploited in the field of optoelectronics due to their enhanced thermal, chemical and environmental stability as well as their physical properties such as high quantum efficiency, efficient charge transport, and semiconducting properties. Carbazole can be used as the host aterials in OLEDs, emissive materials (red, green and blue) in OLEDs, as well as semiconducting materials in organic field effect transistors (OFETs). In this disclosure, carbazole moiety in the cation of GUMBOS can be used to tune the light emission, semiconducting properties and quantum yield.

Coumarins are a broad group of laser dyes with fluorescence emission primarily occurs in the blue-green region of the electromagnetic spectrum (EMS). Coumarins generally have very good quantum yields and photo-stabilities. They are widely used in textile industry, pharmaceutical industry, in blue-green organic dye lasers, and as emissive materials for optoelectroics applications. However, BDC has not been used for blue OLED applications. In this study, BDC is attached to carbazole to extend the conjugated rr electron system to tune the light emission and enhance the photo stability. Ullmann condensation was employed to couple carbazole and BDC with Cu (II) ions as the catalyst and 1,10-phenanthroline as the chelating agent, which has been successfully used to synthesize Imidazole substituted carbazoles. BETI, NTf$_2$ and OTf anions were selected as the counter-anions, as these counter anions contribute significantly to thermal-stability of GUMBOS and may play a significant role to enhance the quantum yields.

Experimental Method

Materials and Reagents.

Carbazole, 3-(2-benzimidazolyl)-7-(diethylamino) coumarin (Coumarin 7, BDC), N-bromosuccinimide, 2-ethylhexyl bromide, copper iodide, sodium hydride, 1,10-phenanthroline, Iodomethane, dimethyl formamide (DMF), tetrahydrofuran (THF), lithium bis(pentafluoroethylsulfonyl) imide (Li BETI), Lithium bis(trifluoromethylsulfonyl) imide (LiNTf$_2$), sodium trifluoromethanesulfonate (Na OTf), tetrabutylammonium hexafluorophosphate (TBAPF$_6$), ferrocene, and deuterated dimethyl sulfoxide (DMSO) were purchased from Sigma-Aldrich (St. Louis, Mo.). Potassium carbonate and anhydrous sodium sulfate were purchased from Fisher Scientific (Fair Lawn, N.J.). Acetonitrile (ACN), hexane, ethyl acetate, dichloromethane (DCM) and methanol were purchased from Macron (Center Valley, Pa.). Silica (particle size 32-63 μm, porosity 60 Å, pH 6.5-7.5) was purchased from Sorbent Technologies (Atlanta, Ga.). Deionized water was obtained from Elga model PURELAB ultra water-filtration system.

Instrumentation.

Absorbance measurements were performed using a UV-3101PC UV-Vis.-NIR scanning spectrophotometer (Shimadzu, Columbia, Md.) with UVProbe 2.43 software. Absorbance measurements were acquired using quartz cuvettes (Starna Cells) with 1 cm path length. Fluorescence emission was measured using a HORIBA Spex Fluorolog-3-spectrofluorimeter (model FL3-22TAU3; Jobin-Yvon, Edison, N.J.). The software used was FluorEssence v3.5. The thin solid films of compounds on quartz were prepared by hand dipping a clean quartz glass into a dilute solution of the compound (1 mM) in THF and dying it in air for 30 minutes. Photo-stability was measured with the same fluorimeter with emission and excitation slit widths at 14 nm. Absolute quantum yields were measured with an integrated sphere (150 mm internal diameter) by connecting fluorimeter to HORIBA Scientific Quanta φ accessory (model FL3-22TAU3; HORIBA Scientific, Edison, N.J.). The software used for absolute quantum yield calculation was sphere correction. Quantum yields and fluorescence measurements were acquired using quartz cuvettes (Starna Cells) with 1 cm and 0.4 cm path lengths, respectively.

Cyclic voltammetry (CV) was performed with an Autolab/EAs 2 computer controlled electrochemical system coupled with a potentiostat (model PGSTAT 302N, Metrohm, Riverview, Fla.). The software used is GPES (version 4.9.007). Three electrodes were used for each CV measurement; a Pt disk electrode as the working electrode (diameter 3 mm), a Pt wire as the counter electrode and an Ag/AgCl non-aqueous electrode as the reference electrode. All electrodes were purchased from CH instruments (Austin, Tex.). Ferrocene was used as the internal reference electrode. TBAPF$_6$ (0.1 M in Acetonitrile) was used as the supporting electrolyte. The scan rate was 0.1 V/s and the potential window was −1.5 V to 2.5 V under stated experimental conditions. The thermal decomposition studies were done with Hi Res Modulated TGA 2950 Thermogravimetric Analyzer TA instrument with temperature ramp 10° C. per minute. X-ray diffraction (XRD) studies were performed with Pananalytical Empyrean X-ray diffractometer. Nuclear magnetic resonance (NMR) spectra were taken using a Bruker AV500 NMR spectrophotometer and mass spectra were taken using Agilent 6210 electrospray time-of-flight mass spectrophotometer.

Synthesis and Characterization

The synthesis protocol was largely adopted from "A New Class of Solid State Ionic Conductors for Application in All Solid State Dye Sensitized Solar Cells" by Midya et al. (*Chemical Communications*, 2010, 46, 2091-2093), which is hereby incorporated by reference in its entirety, and which was developed for the synthesis of imidazole derivatives of carbazoles. "Carbazole-Derived Group of Uniform Materials Based on Organic Salts: Solid State Fluorescent Analogues of Ionic Liquids for Potential Applications in Organic-Based Blue Light-Emitting Diodes" by Siraj et al. (*J. Phy. Chem. C*. 2014, 118, 2312-2320), which is hereby incorporated by reference in its entirety, describes preparation of GUMBOS from imidazole substituted carbazoles. The summarized schematic representation of synthesis protocol with chemical structures is illustrated in FIG. 27A and the detailed protocol for the synthesis of 3,6-diBDC carbazolium iodide (BDCC Iodide) and 3,6-diBDC carbazolium GUMBOS is presented in the Supporting Information section below. See FIG. 38 for exemplary embodiments of carbazole-based GUMBOS.

The three GUMBOS synthesized in this study were 3,6-diBDC carbazolium BETI (BDCC BETI), 3,6-diBDC carbazolium NTf$_2$ (BDCC NTf$_2$), and 3,6-diDBC carbazolium OTf (BDCC OTf). In summary, a mixture of carbazole and N-bromosuccinimide (NBS, approximate molar ratio 1:2) was refluxed to yield 3,6-dibromocarbazole in the step 1 of FIG. 27A. In step 2, 3,6-dibromocarbazole and BDC (approximate molar ratio 1:2) were coupled by copper catalyzed Ullmann condensation in the presence of 1,10-phenanthroline as the chelating agent. The resulting product of 3,6-diBDC carbazole was converted to 3,6-diBDC carbazolium iodide by refluxing 3,6-diBDC carbazole with iodomethane (approximate molar ratio 1:2) in step 3. GUMBOS were synthesized by replacing iodide anion of 3,6-diBDC carbazolium iodide by either OTf, NTf$_2$ or BETI anions using a biphasic ion exchange reaction in step 4. Here, 3,6-diBDC carbazolium iodide was dissolved in DCM (27 µmol, 5 mL) and organic anion (BETI, NTf$_2$ or OTf) was dissolved in minimum amount of water (60 µmol, 1 ml). Then, the water and DCM layers were combined and stirred for 48 hours at room temperature (RT). The products (BDCC BETI, BDCC NTf$_2$, and BDCC OTf) were obtained in the DCM layer after washing the DCM layer thoroughly with DI water. The final synthesis step of BDCC GUMBOS from BDCC iodide is showed in FIG. 27B.

Results

Absorption Spectra.

The normalized UV-Vis absorption spectra of BDCC BETI in THF (curve 2803) and as a thin film on quartz (curve 2806) are shown in FIG. 28A. Absorption spectra of BDCC iodide 2809, BDCC NTf$_2$ 2812 and BDCC OTf 2815 are comparable with these spectra and are shown in FIGS. 28B and 28C, since electron transitions of the cationic moiety not influenced by changing the anion. As shown in FIG. 28C, BDCC BETI have 3 distinguishable peaks with peak maxima at 369, 307 and 241 nm in THF. In the solid film of FIG. 28B, a prominent red shift was observed for the lowest energy peak with $\lambda_{max}$ shifted from 369 to 377 nm with significant peak broadening. These changes can be due to strong intermolecular interactions and aggregation of molecules in the solid state.

The normalized absorption spectra of parent compounds (carbazole 2903 and BDC 2906) and BDCC BETI 2909 in THF are shown in FIG. 29 to illustrate the tuning of absorption in BDCC BETI. Carbazole is an electron deficient molecule. It has 3 absorption peaks (in the wavelength range 250-500 nm) in near UV region with $\lambda_{max}$ at 293 (high intensity), 324 and 336 nm. BDC is an electron rich molecule and has a broad absorbance with $\lambda_{max}$ at 433 nm. Molecular orbitals of BDCC BETI have intermediate energies as a result of extended conjugation of π electron system of these two parent compounds which tuned its absorption to have the main absorption peak lies in an intermediate region with respect to parent compounds with $\lambda_{max}$ at 369 nm.

Fluorescence excitation and emission spectra. Normalized fluorescence excitation spectra 3003 and emission spectra 3006 of 3,6-BDCC BETI in THF are shown in FIG. 30A. Excitation spectra 3009 and emission spectra 3012 of BDCC iodide, BDCC NTf$_2$, and BDCC OTf are comparable with the spectra of FIG. 30A and are shown in FIG. 30B. The emission spectra were recorded at excitation wavelength of 369 nm. A broad emission peak with $\lambda_{max}$ at 424 nm was observed for all the compounds. Excitation spectra were recorded with emission wavelength at 424 nm. Excitation and emission peaks obey the mirror image rule, suggesting no geometrical changes in the excited state. In the emission spectra 3015 of solid film of BDCC BETI, the emission peak is red shifted peak with a peak maximum at 450 nm, as shown in FIG. 30B. This red shift may occur due to the molecular aggregation in the solid phase. In both cases, fluorescence emission of BDCC BETI occurs primarily in blue region of EMS with significant spectral purity, which is highly desirable for blue light emitting OLED applications.

The normalized fluorescence emission of BDCC BETI 3109 with respect to the parent compounds (carbazole 3103 and BDC 3106) in THF are shown in FIG. 31 to illustrate the tuning of the fluorescence emission in BDCC BETI to emit blue light. Carbazole has two emission peaks in the near UV region with $\lambda_{max}$ at 343 and 357 nm. BDC has a single broad emission in the green region of EMS with $\lambda_{max}$ at 478 nm. BDCC BETI has a broad emission peak which lies in the intermediate blue region with respect to parent compounds having $\lambda_{max}$ at 424 nm.

Energy band gap ($E_G$) calculations. $E_G$ is defined as the separation between maximum energy of the valence band and the minimum energy of the conduction band for a given compound. To be used in optoelectronic applications, organic molecules should possess an $E_G$ in the semiconductor range i.e. 0-4 eV. Onset wavelength ($\lambda_{onset}$) of the absorption spectrum is obtained as the wavelength in which the negative tangent drawn to the onset of absorption spectrum intersecting the x axis (wavelength) as shown at 2809 in the FIG. 28. It represents the minimum energy needed to promote a ground state electron to the first excited state. BDCC BETI has a $\lambda_{onset}$ value at 410 nm. Using $E=hc/\lambda$, $E_G$ the value for BDCC BETI was calculated as 3.02 eV. All compounds have $E_G$ values very close to this value (3.02±0.02) confirming they can be used as organic semiconductors. The table of FIG. 32 shows the summary of $E_G$ for the individual compounds.

$E_{HOMO}$ and $E_{LUMO}$ calculations. Electrochemical properties including $E_{HOMO}$ and $E_{LUMO}$ of BDCC materials were obtained by employing cyclic voltammetry. ACN and TBAPF$_6$ (0.1 M) were used as the solvent and the supporting electrolyte. The electrochemical window was determined as −1.0-2.0 V, as illustrated in FIG. 33A. All the compounds showed quasi-reversible cyclic voltammograms with two oxidation peaks within the electrochemical window. First oxidation peak was observed in the range of 0.80-0.85 V and the second was observed the range of 1.30-1.37 V. The first peak may be attributed to carbazole according to the literature. The cyclic voltammograms obtained for BDCC BETI 3303, BDCC NTf$_2$ 3306 and BDCC OTf 3309 are comparable with each other as shown in FIG. 33B. A ferrocene/ferrocinium electrode was used as the internal reference electrode and the $E_{HOMO}$ of the compounds was calculated using:

$$E_{HOMO} = -1e^{-}[E_{anodic\ potential}(V \text{ vs } Fc^+/Fc) + 4.8(V\ Fc^+/Fc \text{ vs zero})]. \quad (7)$$

The ferrocene/ferrocinium peak potential was calculated by averaging the anodic and cathodic peak potentials. The $E_{LUMO}$ was calculated using:

$$E_g(eV) = -(E_{HOMO}(eV) - E_{LUMO}(eV)). \quad (8)$$

The calculated $E_{HOMO}$ and $E_{LUMO}$ values for compounds were 5.03 (±0.03) eV, and 2.01 (±0.02) eV, respectively. The table of FIG. 32 shows the summary of $E_G$ of the individual compounds.

Since carbazole is an electron deficient molecule which is widely used as a hole transport material, the basic design for the OLED device is an assembly of following layers: ITO anode 3403 on a glass substrate, GUMBOS emissive layer 3406, 1,3,5-tris(N-phenylbenzimidazol-2-yl)benzene (TPBI) electron transport layer 3409, and Mg:Ag cathode 3412. An example of the basic design is schematically presented in FIG. 34. The $E_{LUMO}$ of the GUMBOS lie well above TPBI (−2.7 eV), as well as many other common electron transport layers such as tris(8-hydroxyquinolinato) aluminum (Alq$_3$, −3.0 eV), aluminum (III) bis(2-methyl-8-quinolinato)-4-phenlphenolate (BAlq, −3.0 eV), which is important for the efficient electron transport in the basic design for commercial utilization of these materials.

Photo-Stability.

Photo-stability is the resistance of a compound towards undesirable photochemical changes including polymerization, photo-induced decomposition etc. These changes affect chemical, electronic, and spectral properties. The relative intensity (I/I$_0$) vs. time graphs are shown in FIG. 35. BDCC iodide 3503 and BDCC GUMBOS (BETI 3506, NTf$_2$ 3509 and OTf 3512) were tested for photo-stability by irradiating dilute solutions in THF (1 μM) at 367 nm, while measuring fluorescence emission intensity at 424 nm for 2000 seconds. All the compounds showed remarkable photo-stability. BDCC BETI 3506 and BDCC NTf$_2$ 3509 did not show any measurable loss of relative emission intensity. BDCC iodide 3503 and BDCC OTf 3512 showed only 7 and 4 percent reductions in relative emission intensity, respectively. Observed high photostability of BDC carbazole compounds may be attributed to the extended conjugation of it electron systems of the cation, which have the ability to effectively absorb the photon energy without degrading.

Thermogravimetric Studies.

Resistance to thermal degradation is an important factor for determining the lifetime as well as the robustness of optoelectronic devices. Prevention of localized heat generation of the device by reducing the electrical stress as well as the thermionic emission is also important to maintain the heat generation in negligible levels (less than 25° C.). TGA curves were used to determine the decomposition temperatures of the BDC carbazole compounds. The compounds were steadily heated (from 0° C. to 600° C.) in inert atmosphere at a rate of 10° C. per minute. The resultant TGA curves are shown in FIG. 36. All the compounds showed single step decomposing mechanism. BDCC iodide 3603 has the lowest decomposition temperature of 188° C. BDCC BETI 3606, BDCC NTf$_2$ 3609 and BDCC OTf 3612 have decomposition temperatures (T$_D$) of 311, 308 and 255° C., respectively. As can be seen, the thermal stability increased in the GUMBOS 3606-3612 with respect to BDCC iodide 3603. High thermal stability of organic anions may positively influence the thermal stability of the overall compound by enhancing interionic interactions. The decomposition temperatures of BDCC BETI 3606 and BDCC NTf$_2$ 3609 were very close and higher than BDCC OTf 3612.

Quantum yield (QY).

Quantum yield is defined as the ratio of the emitted photons to excited photons. For OLED applications, emissive materials with good quantum yields are important to enhance the overall efficiency of the optoelectronic device. The quantum yield of a compound can be measured experimentally as absolute quantum yield (Abs. QY) according to:

$$\text{Abs} \cdot QY = \frac{\substack{\text{\# Photons emitted by the compound} - \\ \text{"Dark signal" in the emission area of the compound}}}{\substack{\text{\# Incident photons} - \\ \text{\# Photons not absorbed by the compound}}} = \frac{\substack{\text{Integ. emission peak of the compound} - \\ \text{Integ. dark signal in the emission area from blank}}}{\substack{\text{Integ. incident light signal from blank} - \\ \text{Integ. incident light signal with the compound}}}, \quad (9)$$

using an integrated sphere as well as relative to a reference compound (Rel. QY) according to:

$$Rel \cdot QY = \quad (10)$$
$$\phi(\text{reference}) = \frac{E(\text{analyte})}{E(\text{reference})} = \frac{A(\text{reference})}{A(\text{analyte})} * \frac{N(\text{analyte})}{N(\text{reference})},$$

where, ϕ(reference) is the quantum yield of the reference reported in literature with the same solvent, E (analyte) is the integrated area of the emission spectrum from the analyte, E (reference) is the integrated area of the emission spectrum from the reference compound, A (analyte) is the absorption intensity of the analyte (at a common wavelength for both analyte and reference, close to their absorption maxima and both have very close absorption intensities), A (reference) is the absorption intensity of the reference at the selected wavelength, N (analyte) is the refractive index of the analyte solution, N (reference) is the refractive index of the reference solution.

In Equation (10), the refractive indices of analytes and references can be assumed to be the same for dilute solutions in the same solvent. BDC was used as the reference compound, which has absolute quantum yield of 0.67 in acetonitrile. The quantum yields were calculated using both methods and BDCC BETI was found to have the highest quantum yield of 96%. BDCC OTf, BDCC NTf$_2$ and BDCC iodide had quantum yields of 91, 87 and 90% respectively.

XRD Studies.

It is beneficial to reduce the degree of crystallinity for light emissive organic materials used in optoelectronic devices due to the anisotropy and other non-linear optical characteristics associated with the crystal structures. In order to determine the degree of crystallinity, X-ray diffraction (XRD) was employed to BDCC iodide and FIG. 37 shows the resultant X-ray crystallograph. The complete absence of peaks provides evidence of the amorphous nature of the material. Since incorporation of bulky anions such as OTf, NTf$_2$ and BETI will further reduce the packing of the molecules, it is assumed that BDCC GUMBOS should be amorphous.

Conclusion

Coumarin substituted carbazole based GUMBOS (BDCC BETI, BDCC NTf$_2$, BDCC OTf) were successfully synthesized and their photochemical properties were investigated. These compounds showed electronic properties suitable for use as semiconducting materials in optoelectronics. Also fluorescence emission characteristics suggested that these compounds can emit light in the blue region of the EMS with above 90% quantum yields in the case of BDCC BETI. These GUMBOS showed remarkable stability towards light and reasonable stability towards thermal degradation. The study indicates good potential as emitting materials in optoelectronics.

Supporting Information

Synthesis of 3,6-dibromocarbazole

Carbazole (1.0 g, 6 mmol) was added to anhydrous DMF (15 mL) at room temperature while stirring. The resulting mixture was stirred at room temperature for another 15 minutes. N-bromosuccinimide (2.3 g, 13 mmol) in anhydrous DMF (10 mL) was added drop wise to carbazole-DMF mixture at 0° C. in inert atmosphere. The resulting solution was allowed to reach to the room temperature and continued stirring for another 2 hours. This solution was poured to DI water. The milky white precipitate formed was filtered and dissolved in DCM. DCM layer was washed with water several times. Then DCM layer was dried with anhydrous sodium sulfate and solvent was removed under high vacuum. Resultant white solid was recrystallized using ethanol to get light brown silvery flake-like 3,6-dibromocarbazole crystals (1.1 g, 55% yield).

MS, ESI-m/z 323 (M+);
$^1$H NMR (Deuterated DMSO, 5 00 MHz, ppm): δ 11.49 (S, 1H), 8.08-8.10 (D, 2H), 7.72 (S, 2H), 7.32-7.34 (D, 2H).

Synthesis of 3,6-BDC carbazole

A mixture of 3,6-dibromocarbazole (543 mg, 1.6 mmol), BDC (1.1 g, 3.3 mmol), 1, 10-phenanthroline (65 mg, 0.36 mmol), Copper iodide (31 mg, 0.166 mmol) and potassium carbonate (575 mg, 0.0042 mmol) in anhydrous DMF (25 mL) was stirred for 30 minutes at room temperature and then refluxed at 150° C. with $N_2$ atmosphere for 48 hours and cooled to room temperature. DMF was removed under high vacuum. The resulting brown solid washed with water and extracted with DCM. The organic fraction was dried with anhydrous sodium sulfate and the solvent was removed under reduced pressure. The resulting dark brown solid was purified using a silica column with 1:1 ethyl acetate:hexane as the eluent. Evaporation of solvent yields the purified compound as a brown solid (0.9 g, 68% yield).

MS, ESI-m/z 829 (M+);
$^1$H NMR (Deuterated DMSO, 5 00 MHz, ppm): δ 12.28 (S, 1H), 8.92 (S, 2H), 8.09-8.11 (D, 2H), 7.70-7.72 (M, 4H), 7.60-7.63 (D, 4H), 7.32-7.34 (DD, 2H), 7.16-7.18 (M, 4H), 6.81-6.83 (DD, 2H), 6.66-6.67 (D, 2H), 3.37-3.51 (Q, 8H), 1.15-1.18 (T, 12H).

Synthesis of 3,6-(N-methyl)BDC carbazolium Iodide 3,6-BDC carbazole (415 mg, 0.5 mmol) was dissolved in DMF (15 mL). Iodomethane (312 mg, 2.2 mmol) was introduced to 3,6-BDC carbazole and refluxed at 60° C. for 24 hours in an inert atmosphere. DMF was removed under high vacuum. The resulting brown solid was purified using a silica column with 1:9 methanol:DCM as the eluent. Evaporation of solvent yields the purified compound as a light brown solid (380 mg, 68% yield).

MS, ESI-m/z 857 (M+);
$^1$H NMR (Deuterated DMSO, 500 MHz, ppm): δ 11.52 (S, 1H), 8.30 (S, 2H), 8.09-8.11 (D, 2H), 7.58-7.72 (M, 6H), 7.23-7.34 (M, 5H), 6.79-6.82 (D, 2H), 6.64-6.65 (D, 2H), 3.73 (S, 6H), 3.47-3.52 (Q, 8H), 1.15-1.18 (T, 12H).

Synthesis of 3,6-(N-methyl)BDC carbazolium GUMBOS 3,6-(N-methyl)BDC carbazolium iodide (25 mg, 27 μmol) was anion exchanged with Li BETI (23 mg, 60 μmol)/Li $NTf_2$ (17 mg, 60 μmol)/Na OTf (11 mg, 60 μmol) in a biphasic solution where 3,6-(N-methyl)BDC carbazolium iodide was dissolved in DCM (5 mL) while a saturated solution of Li-BETI was prepared using minimum amount of water. This biphasic solution of DCM and water was stirred for 2 days. Then DCM layer containing the product was separated and washed with water. DCM was evaporated under high vacuum followed by freeze drying. BDCC BETI (40 mg, 91%), BDCC $NTf_2$ (34 mg, 89%), BDCC OTf (29 mg, 94%); BDCC BETI-MS,ESI$^+$-m/z 857 (M$^+$) MS,ESI$^-$ (M$^-$)-m/z 380; BDCC $NTf_2$-MS,ESI$^+$-m/z 857 (M$^+$) MS,ESI-280 (M$^-$); BDCC OTf-MS,ESI$^+$-m/z 857 (M$^+$) MS,ESI (M$^-$)–149;

$^1$H NMRs for all 3 compounds similar to that of BDCC iodide in Step 3; $^{19}$F NMR for BDCC BETI: (Deuterated DMSO, 500 MHz, ppm): δ-117.24 (S, 4F), −78.94 (S, 6F);
$^{19}$F NMR for BDCC $NTf_2$: (Deuterated DMSO, 500 MHz, ppm): δ-77.75 (S, 6F); $^{19}$F NMR for BDCC OTf: (Deuterated DMSO, 500 MHz, ppm): 6-78.72 (S, 3F).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

Therefore, at least the following is claimed:
1. A composition, comprising:
   a solid phase carbazole-based GUMBOS (group of uniform materials based on organic salts) comprising a carbazole-based counterion.
2. The composition of claim 1, wherein the carbazole-based counterion is selected from the group consisting of trifluoromethanesulfonate ([OTf]), bis-(trifluoromethanesulfonyl)imide ([NTf$_2$]), bis-(pentafluoroethylsulfonyl)imide ([BETI]), tetrafluoroborate (BF4), hexafluorophosphate (PF6), and thiocyanate (SCN).

3. The composition of claim 1, wherein the solid phase carbazole-based GUMBOS comprises an imidazole group or (alkyl)imidazole group at a 3-, 6-, or N-position of a carbazole unit.

4. The composition of claim 3, wherein the (alkyl)imidazole group is a (methyl) imidazole group at the 3-position of the carbazole unit.

5. The composition of claim 3, wherein the imidazole group is at the 3-position of the carbazole unit.

6. The composition of claim 1, wherein the solid phase carbazole-based GUMBOS has a fluorescence quantum yield of about 73% or greater.

7. The composition of claim 6, wherein the solid phase carbazole-based GUMBOS has a fluorescence quantum yield of about 94% or greater.

8. The composition of claim 7, wherein the solid phase carbazole-based GUMBOS has a fluorescence quantum yield of about 99% or greater.

9. The composition of claim 1, wherein the solid phase carbazole-based GUMBOS has a thermal decomposition temperature (Td) in a range from about 350° C. to about 450° C.

10. The composition of claim 1, wherein the solid phase carbazole-based GUMBOS comprises carbazoleimidazolium trifluoromethanesulfonate [CI][OTf], carbazoleimidazolium bis-(trifluoromethylsulfonyl)imide [CI][NTf$_2$], or carbazoleimidazolium bis(pentafluoroethylsulfonyl)imide [CI][BETI].

11. The composition of claim 1, wherein the solid phase carbazole-based GUMBOS comprises 3,6-diBDC carbazolium trifluoromethanesulfonate [BDCC OTf], 3,6-diBDC carbazolium bis-(trifluoromethylsulfonyl)imide [BDCC NTf$_2$], or 3,6-diBDC carbazolium bis(pentafluoroethylsulfonyl)imide [BDCC BETI].

12. The composition of claim 1, wherein the solid phase carbazole-based GUMBOS exhibits radiative emission from a second excited singlet state.

13. The composition of claim 12, wherein the solid phase carbazole-based GUMBOS further exhibits radiative emission from a first excited singlet state.

14. The composition of claim 12, wherein an energy gap between a first excited singlet state of the solid phase carbazole-based GUMBOS and the second excited singlet state is greater than 6000 cm$^{-1}$.

15. An organic light emitting diode (OLED), comprising an active layer including the solid phase carbazole-based GUMBOS of claim 1.

16. The OLED of claim 15, wherein the active layer is disposed between a first electrode and a second electrode.

17. The OLED of claim 16, wherein the active layer comprises a GUMBOS emission layer and an electron transport layer.

18. A method, comprising:
preparing a biphasic solution comprising carbazoleimidazolium iodide (CII) dissolved in dichloromethane (DCM) and a dissolved salt comprising a sodium salt or a lithium salt;
separating a layer of DCM from the biphasic solution after stirring;
washing the DCM with water to remove byproducts; and
evaporating the DCM to form a solid phase carbazoleimidazole-based GUMBOS (group of uniform materials based on organic salts).

19. The method of claim 18, wherein the dissolved salt comprises sodium trifluoromethanesulfonate (NaOTf) dissolved in deionized water.

20. The method of claim 19, wherein the solid phase carbazoleimidazole-based GUMBOS comprises carbazoleimidazolium trifluoromethanesulfonate [CI][OTf].

21. The method of claim 18, wherein the dissolved salt comprises lithium bis(trifluoromethylsulfonyl)imide (LiNTf$_2$) or lithium bis-(pentafluoroethylsulfonyl)imide (Li-BETI) dissolved in deionized water.

22. The method of claim 21, wherein the solid phase carbazoleimidazole-based GUMBOS comprises carbazoleimidazolium bis-(trifluoromethylsulfonyl)imide [CI][NTf$_2$] or carbazoleimidazolium bis(pentafluoroethylsulfonyl)imide [CI][BETI].

23. The method of claim 18, wherein the solid phase carbazoleimidazole-based GUMBOS is based upon anion exchange of N-Ethylhexyl-3-imidazolium carbazole.

24. The method of claim 18, wherein the biphasic solution was stirred for 3-4 days.

25. The method of claim 18, further comprising freeze drying the solid phase carbazoleimidazole-based GUMBOS.

* * * * *